United States Patent
Doverspike et al.

(10) Patent No.: US 11,998,513 B2
(45) Date of Patent: Jun. 4, 2024

(54) TWO-PART NITRIC OXIDE GENERATING TOPICAL COMPOSITIONS

(71) Applicant: THE REGENTS OF THE UNIVERSITY OF MICHIGAN, Ann Arbor, MI (US)

(72) Inventors: Joshua C. Doverspike, Ann Arbor, MI (US); James Phan, Lake Orion, MI (US); Jianfeng Wu, Canton, MI (US); Chuanwu Xi, Ann Arbor, MI (US); Yu Qin, Ann Arbor, MI (US); Mark E. Meyerhoff, Ann Arbor, MI (US); Yang Zhou, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 920 days.

(21) Appl. No.: 16/976,382

(22) PCT Filed: Feb. 28, 2019

(86) PCT No.: PCT/US2019/019988
§ 371 (c)(1),
(2) Date: Aug. 27, 2020

(87) PCT Pub. No.: WO2019/169092
PCT Pub. Date: Sep. 6, 2019

(65) Prior Publication Data
US 2020/0405658 A1 Dec. 31, 2020

Related U.S. Application Data

(60) Provisional application No. 62/637,008, filed on Mar. 1, 2018.

(51) Int. Cl.
| | | |
|---|---|---|
| *A61K 31/04* | (2006.01) | |
| *A61K 31/198* | (2006.01) | |
| *A61K 33/30* | (2006.01) | |
| *A61K 38/06* | (2006.01) | |
| *A61K 47/06* | (2006.01) | |
| *B01J 23/72* | (2006.01) | |
| *B01J 31/02* | (2006.01) | |
| *A61K 9/00* | (2006.01) | |
| *A61K 9/06* | (2006.01) | |

(52) U.S. Cl.
CPC ............ *A61K 31/04* (2013.01); *A61K 31/198* (2013.01); *A61K 33/30* (2013.01); *A61K 38/063* (2013.01); *A61K 47/06* (2013.01); *B01J 23/72* (2013.01); *B01J 31/0272* (2013.01); *A61K 9/0014* (2013.01); *A61K 9/06* (2013.01)

(58) Field of Classification Search
CPC .............................. A61K 31/04; A61K 31/095
See application file for complete search history.

(56) References Cited

U.S. PATENT DOCUMENTS

| | | |
|---|---|---|
| 7,678,391 B2 | 3/2010 | Graham et al. |
| 2002/0187990 A1 | 12/2002 | Parks et al. |
| 2006/0198883 A1 | 9/2006 | Parks et al. |
| 2008/0045909 A1 | 2/2008 | Fossel |
| 2013/0330244 A1 | 12/2013 | Balaban et al. |

FOREIGN PATENT DOCUMENTS

| | | |
|---|---|---|
| WO | WO 2008/153762 | 12/2008 |
| WO | WO 2017/147295 | 8/2017 |

OTHER PUBLICATIONS

"Desitin Rapid Relief Diaper Rash-Zinc Oxide Cream", Johnson & Johnson Consumer Inc., Nov. 2017, retrieved from https://dailymed.nlm.nih.gov/dailymed/getFile.cfm?setid=60dcadb9-6a63-452c-9d78-ffa62e6d37f2 on Apr. 15, 2019, 6 pages.
International Search Report and Written Opinion for International Application No. PCT/US2019/019988 dated May 6, 2019, 10 pages.

*Primary Examiner* — Deepak R Rao
(74) *Attorney, Agent, or Firm* — Dierker & Kavanaugh, P.C.

(57) ABSTRACT

A two-part topical composition includes a first composition including a S-nitrosothiol nitric oxide donor and a carrier, and a second composition including zinc oxide. The second composition is to be mixed with the first composition. The zinc oxide reacts with the S-nitrosothiol nitric oxide donor at a temperature ranging from about 20° C. to about 40° C. to enhance a rate of release of nitric oxide from a mixture of the first composition and the second composition.

19 Claims, 23 Drawing Sheets

1 HOUR　　　　　　　　　　2 HOURS

3 HOURS　　　　　　　　　　4 HOURS

5 HOURS　　　　　　　　　　CONTROL

1 HOUR

2 HOURS

3 HOURS

4 HOURS

5 HOURS

CONTROL

No CREAM

NO-RELEASING CREAM

CONTROL CREAM

TWO-PART NITRIC OXIDE GENERATING TOPICAL COMPOSITIONS

CROSS-REFERENCE TO RELATED APPLICATIONS

This application claims the benefit of U.S. provisional application Ser. No. 62/637,008, filed Mar. 1, 2018, the contents of which is incorporated by reference herein in its entirety.

BACKGROUND

Nitric oxide is the endothelium-derived relaxing factor (EDRF) that causes relaxation of smooth muscle cells located in blood vessel walls. This effect causes vasodilation, increasing blood flow to body tissues, and lowers blood pressure. Nitric oxide (NO) also has been shown to have several other important physiological functions, including cancer-fighting potency, increasing angiogenesis, i.e. proliferation of new blood vessels (for potential wound healing applications), anti-platelet activity, and anti-microbial/anti-viral activity. In some instances, NO can be used as a therapeutic agent, for example, to control infection, prevent biofilm formation, and minimize inflammation and fibrosis.

BRIEF DESCRIPTION OF THE DRAWINGS

Features of examples of the present disclosure will become apparent by reference to the following detailed description and drawings.

FIG. 2A shows the NO release (in parts per billion, ppb) over time (in minutes), and FIG. 2B shows the cumulative NO release (in ppb) over time (in minutes);

FIG. 3A shows the NO release (in ppb) over time (in hours), and FIG. 3B shows the cumulative NO release (in ppb) over time (in hours);

FIG. 11A shows the real-time NO release over time (nmol NO/mg sample versus hours), and FIG. 11B shows the cumulative NO release over time (nmol NO/mg sample versus hours) (data represents the mean±SEM (n=3));

DETAILED DESCRIPTION

Figure 1:
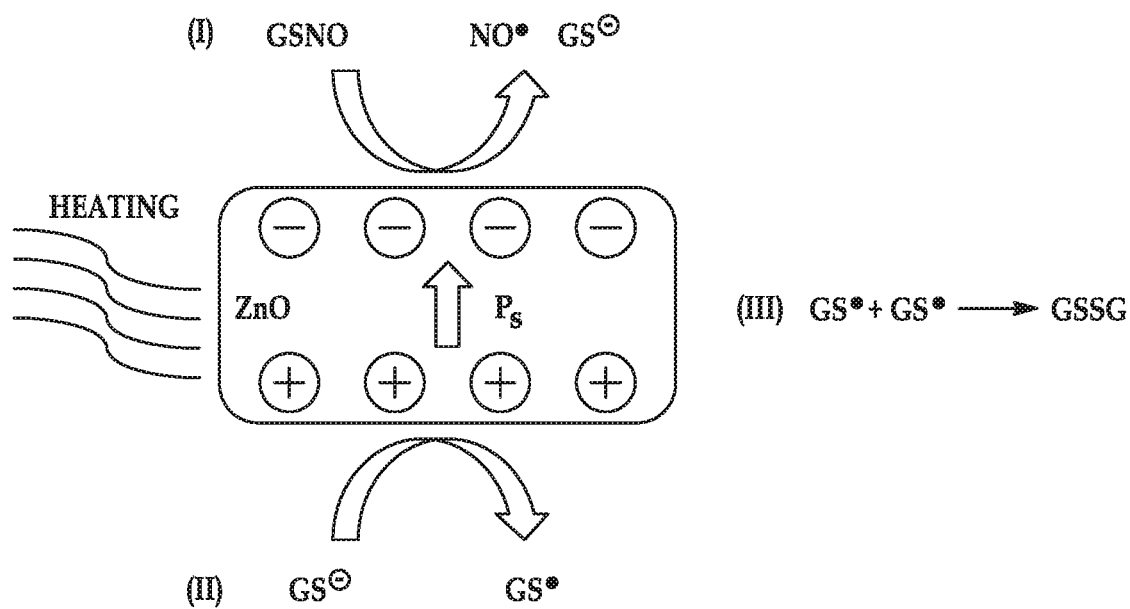
FIG. 1 is a schematic diagram illustrating the proposed mechanism of nitric oxide release from one example of the two-part topical composition disclosed herein.

Disclosed herein are two-part topical compositions that release nitric oxide. Nitric oxide has potent antimicrobial, antiviral, and anti-inflammatory properties that may be beneficial in the topical treatment of dermal conditions. Beyond these properties, the nitric oxide may also promote angiogenesis, which may be advantageous for wound healing. The two-part topical compositions disclosed herein may be suitable for treating a variety of dermal conditions, such as acne, foot ulcers in diabetic patients, skin wounds, or the like.

In the two-part topical compositions disclosed herein, one composition includes a S-nitrosothiol nitric oxide donor and a carrier, and the other composition contains an accelerant that initiates NO release from the S-nitrosothiol nitric oxide donor when the two compositions are mixed together and heated to a temperature ranging from about 20° C. to about 40° C. In some examples, the mixture of the two compositions is headed to a temperature of skin (e.g., ranging from about 24° C. to about 40° C. or from about 30° C. to about 40° C.). As such, in one example, the two-part topical composition includes the first composition including the S-nitrosothiol nitric oxide donor and the carrier, and the second composition including zinc oxide, wherein the second composition is to be mixed with the first composition, and wherein the zinc oxide is to react with the S-nitrosothiol nitric oxide donor at a temperature ranging from about 20° C. to about 40° C. to release nitric oxide from a mixture of the first composition and the second composition.

One (i.e., the first) of the compositions includes the S-nitrosothiol nitric oxide donor and the carrier. In an example, the S-nitrosothiol nitric oxide donor is an S-nitrosothiol selected from the group consisting of S-nitrosoglutathione (GSNO, an endogenous species found in blood):

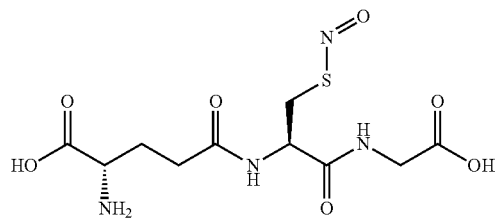 [SMILES: N[C@@H](CCC(=O)N[C@@H](CSN=O)C(=O)NCC(=O)O)C(=O)O]

S-nitroso-n-acetylpenicillamine (SNAP):

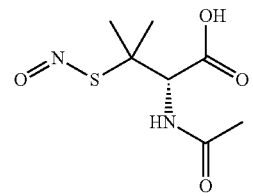

and combinations thereof.

The S-nitrosothiol nitric oxide donor may be in the form of a fine powder. In an example, GSNO or SNAP crystals may be ground into powder form before being mixed with the hydrophobic carrier.

The carrier of the S-nitrosothiol is a relatively hydrophobic carrier that substantially prevents S-nitrosothiol degradation during long-term storage, and is able to release NO upon introduction of the other composition that contains the accelerant. In an example, the carrier is petroleum jelly. Petroleum jelly has an extremely hydrophobic nature, in part because it consists of saturated hydrocarbons. Petroleum jelly has been found to be a stable carrier of GSNO for at least 300 days at room temperature (e.g., from 18° C. to about 25° C.), and has been found to be a stable carrier of SNAP for at least 2 months with higher amounts of SNAP (e.g., 10 wt % SNAP) and for at least 6 months with lower amounts of SNAP (e.g., 5 wt % SNAP) at room temperature. In another example, the carrier is a combination of petroleum jelly (e.g., commercially available as VASELINE®) and an ointment (e.g., commercially available as NEOSPORIN®) including bacitracin, neomycin, and polymyxin B, in a relatively low-molecular-weight base of cocoa butter, cottonseed oil, sodium pyruvate, tocopheryl acetate, and petroleum jelly. With this combination, the carrier may include a weight ratio of petroleum jelly to the other ointment ranging from about 5:95 to about 99:1. It is to be understood that other hydrophobic carriers may be used, as long as they can stably store the S-nitrosothiol and release NO from the S-nitrosothiol when combined with the accelerant-containing composition and heated, for example, to body temperature. In some examples, the hydrophobic carrier has a water content (by weight) of 5% or less. In still other examples, the hydrophobic carrier has a water content (by weight) of 0 wt % to about 1 wt %.

In some examples of the first composition, the S-nitrosothiol is selected from the group consisting of S-nitroso-n-acetylpenicillamine, S-nitrosoglutathione, and combinations thereof; and the carrier is petroleum jelly.

In an example, the concentration of the S-nitrosothiol nitric oxide donor in the first composition ranges from about 2.5 wt % to about 40 wt %, based on the total weight of the first composition. In a more specific example, GSNO may be present in the first composition in an amount ranging from about 5 wt % to about 40 wt %, based on the total weight of the first composition. In another more specific example, SNAP may be present in the first composition in an amount ranging from about 2.5 wt % to about 35 wt %, based on the total weight of the first composition.

The viscosity of the first composition may be 5 cSt or more (measured at 25° C.).

The first composition may be prepared by adding a desired amount of the S-nitrosothiol nitric oxide donor to the carrier and mixing the two components.

The other (i.e., second) of the compositions contains the accelerant that initiates NO release from the S-nitrosothiol nitric oxide donor when the two compositions are mixed together and heated. In the examples disclosed herein, it has been found that zinc oxide is a suitable accelerant, or more particularly, a reactant. When combined with the first composition and heated, the zinc oxide acts as a thermoelectric or pyroelectric material, and can perform thermocatalysis at temperature slightly above room temperature. As the zinc oxide heats up from the temperature of the skin to which it is applied, it forms an electric voltage at its surface that can help reduce the S-nitrosothiol (e.g., GSNO or SNAP) into NO, and enhance the rate of NO release. FIG. 1 depicts a schematic illustration of a proposed mechanism of the NO release from GSNO in the presence of zinc oxide. As shown in FIG. 1, when the zinc oxide is heated (e.g., to a temperature ranging from about 20° C. to about 40° C.), the polarization density decreases ($\Delta Ps<0$) causing uncompensated charges (both positive and negative) on the surface. It is believed that the negative charges reduce the GSNO to produce NO and GSH (i.e., glutathione) (step I in FIG. 1). After GSH is produced, the positive charge on the zinc oxide surface is able to oxidize the GSH to form GS. (step II in FIG. 1). Then, two GS. can combine to form the disulfide GSSG (step III in FIG. 1).

In addition to accelerating NO release, the zinc oxide is also an antimicrobial. As such, the combination of the zinc oxide with the nitric oxide enhances the overall antimicrobial effect of the mixture formed when the components of two-part topical composition are combined.

Zinc oxide may be present in the second composition in the form of nanoparticles. The nanoparticles may have an average particle size ranging from about 10 nm to about 100 nm. In one example, the zinc oxide nanoparticles have an average particle size of about 30 nm. The average particle size may represent the mean value for a distribution of particles, which may be associated with the basis of the distribution calculation (number, surface, or volume). As such, in some examples, the average particle size may represent a volume mean diameter, a number mean diameter, or a surface mean diameter. The average particle size may be determined using a particle size analyzer, or using X-ray diffraction (XRD), scanning electron microscopy (SEM), transmission electron microscopy (TEM), etc.

In addition to the zinc oxide, the second composition may also include glycerin/glycerol. It is believed that glycerin/glycerol may further contribute to the NO release. In some examples, in addition to the zinc oxide, the second composition may also include mineral oil, petrolatum, beeswax, dimethicone, sorbitan sesquioleate, microcrystalline wax, PEG-30 dipolyhydroxystearate, aloe barbadensis leaf extract, glycerin (i.e., glycerol), tropolone, tocopheryl acetate, 1,2-hexanediol, caprylyl glycol, magnesium sulfate, potassium hydroxide, and phenoxyethanol. When the second composition includes the listed components, the commercially available cream, DESITIN®, may be used. It is to be understood, however, that another commercially available zinc oxide containing cream similar to DESITIN® may also be used as the second composition.

In an example, the concentration of the zinc oxide in the second composition ranges from about 5 wt % to about 40 wt %, based on the total weight of the second composition. In another example, zinc oxide may be present in the second composition in an amount ranging from about 10 wt % to about 20 wt %, based on the total weight of the second composition. In still another example, zinc oxide may be present in the second composition in an amount ranging from about 12 wt % to about 15 wt %, based on the total weight of the second composition. In still another specific example, zinc oxide may be present in the second composition in an amount of about 13 wt %, based on the total weight of the second composition.

In some examples, the second composition may further include a copper or an organoselenium catalyst. Both copper and the organoselenium may be a catalyst for the release of NO from SNAP and/or GSNO, and thus may be included to further enhance the release rate of NO when the first composition is combined with the second composition. In an example, the copper catalyst may be copper(II) sulfate ($CuSO_4$). In another example, the organoselenium catalyst may be carboxyl-ebselen, seleocystamine, 3,3'-dipropionic-diselenide, ebselen, ebselen-PEI, or combinations thereof. In the mixture of the first and second compositions, it may be desirable for the catalyst to be present in an amount ranging from about 0.5 wt % to about 4 wt %, based on a total weight of the mixture. As such, the amount of the catalyst in the second composition may range from about 0.625 wt % to about 5 wt %.

The first and second compositions may be mixed together just prior to being applied to skin, where the mixture is heated due, in part, to the mixing and to the temperature of the skin. Maintaining the compositions separately prior to use keeps the zinc oxide from prematurely reacting to release NO. This helps to ensure that the NO is generated and released to the desirable area where the mixture of the compositions is applied.

The first and second compositions may be mixed in effective amounts that generate nitric oxide. In an example, the effective amounts of the first composition to the second composition correspond to a weight ratio ranging from about 2:98 to about 95:5. In another example, the weight ratio of the first composition to the second composition ranges from about 50:50 (i.e., 1:1) to about 20:80 (i.e., 1:4). In one specific example, the mixture includes the first composition and the second composition at a weight ratio of 27.3:72.7. In another specific example, the mixture includes the first composition and the second composition at a weight ratio of 27:73. It has been found that at these ratios, a suitable amount of zinc oxide is available for reacting to generate nitric oxide for a desirable time period and at desirable levels.

In an example, the two-part topical composition is part of a topical composition kit. In an example, the topical composition kit comprises a first container having therein the first composition including the S-nitrosothiol nitric oxide donor and the carrier; and the second container having therein the second composition including zinc oxide, the second composition to be mixed with the first composition; wherein the first and second containers respectively deliver effective amounts of the first and second compositions, wherein the zinc oxide reacts with the S-nitrosothiol nitric oxide donor at a temperature ranging from about 20° C. to about 40° C. to release nitric oxide from a mixture of the first composition and the second composition.

In one example, the containers are syringes that deliver the effective amounts of the respective compositions when the plungers are depressed. In another example, the containers are tubes. In this example, the tubes may come with a dosing card (e.g., a clear polypropylene sheet). The dosing card may include marked areas for each of the first and second compositions, and the marked areas correspond with an appropriate dosage of each of the compositions to obtain a mixture with the desired amounts of S-nitrosothiol and zinc oxide. In still another example, the containers may be bottles or other storage mechanisms from which the compositions can be retrieved. In these still other examples, the kit may come with a dosing stick, spoon, or the like which correspond with an appropriate dosage of each of the compositions to obtain a mixture with the desired amounts of S-nitrosothiol and zinc oxide.

The containers may be opaque, so that the first and second compositions are not exposed to light during storage. For the first composition, this type of container can help to reduce, or even prevent, photochemical decomposition of the S-nitrosothiol.

In the topical composition kit, it is to be understood that any example of the first cream and any example of the second cream disclosed herein may be used.

Examples of the mixture formed of the first composition and the second composition mixed at a weight ratio of about 50:50 may include the S-nitrosothiol in an amount ranging from about 1.25 wt % to about 20 wt % of the total weight of the mixture, and may include the zinc oxide in an amount ranging from about 2.5 wt % to about 20 wt % of the total weight of the mixture. Examples of the mixture formed of the first composition and the second composition mixed at a weight ratio of about 20:80 may include the S-nitrosothiol in an amount ranging from about 0.5 wt % to about 8 wt % of the total weight of the mixture, and may include the zinc oxide in an amount ranging from about 4 wt % to about 32 wt % of the total weight of the mixture. The concentration of the respective components in the mixture will depend, in part, upon the amount in the first composition or the second composition and the weight ratio at which the two compositions are mixed.

A method for regulating nitric oxide release from a topical composition is also disclosed herein. The method includes mixing an effective amount of the first composition (including the S-nitrosothiol nitric oxide donor and the carrier) with an effective amount of the second composition (including zinc oxide) to form a mixture, and heating the mixture to a temperature ranging from about 20° C. to about 40° C. Heating may be accomplished by applying the mixture to skin, and the temperature of the skin alone may heat the mixture. The mixture may also be rubbed on the skin, and rubbing may further contribute to heating up the mixture. As previously described, heating causes the zinc oxide to perform thermocatalysis, where generated charges at the surface of the zinc oxide are capable of reducing the S-nitrosothiol (e.g., GSNO or SNAP) to form NO.

A method for treating a skin ailment, such as acne, skin ulcers, or other dermal wounds, is also disclosed herein. The method includes mixing an effective amount of the first composition (including the S-nitrosothiol nitric oxide donor and the carrier) with an effective amount of the second composition (including zinc oxide) to form a mixture, and applying the mixture to skin, whereby the mixture is heated to a temperature ranging from about 20° C. to about 40° C. and the zinc oxide reacts with the S-nitrosothiol nitric oxide donor to release NO. As mentioned above, heating is accomplished through the application of the mixture to the skin. As such, heating may be the result of result heat transfer from the skin to the mixture applied thereto. As noted above, heating may be further enhanced by rubbing the mixture onto/into the skin. Also as previously described, heating causes the zinc oxide to perform thermocatalysis, where generated charges at the surface of the zinc oxide are capable of reducing the S-nitrosothiol (e.g., GSNO or SNAP) to form NO. The NO penetrates into the skin, where it can inhibit growth of microbials and/or viruses, reduce inflammation, and/or promote angiogenesis, and thus treat a particular dermal condition.

In some examples, the mixture of the first and second compositions may be applied to the skin once or twice daily.

In any of the example methods disclosed herein, any example of the first composition may be combined with any example of the second composition to form the mixture. Also in any of the example methods disclosed herein, any of the containers may be used to store the respective compositions.

To further illustrate the present disclosure, examples are given herein. It is to be understood that these examples are provided for illustrative purposes and are not to be construed as limiting the scope of the present disclosure.

Example 1

Figure 2A:
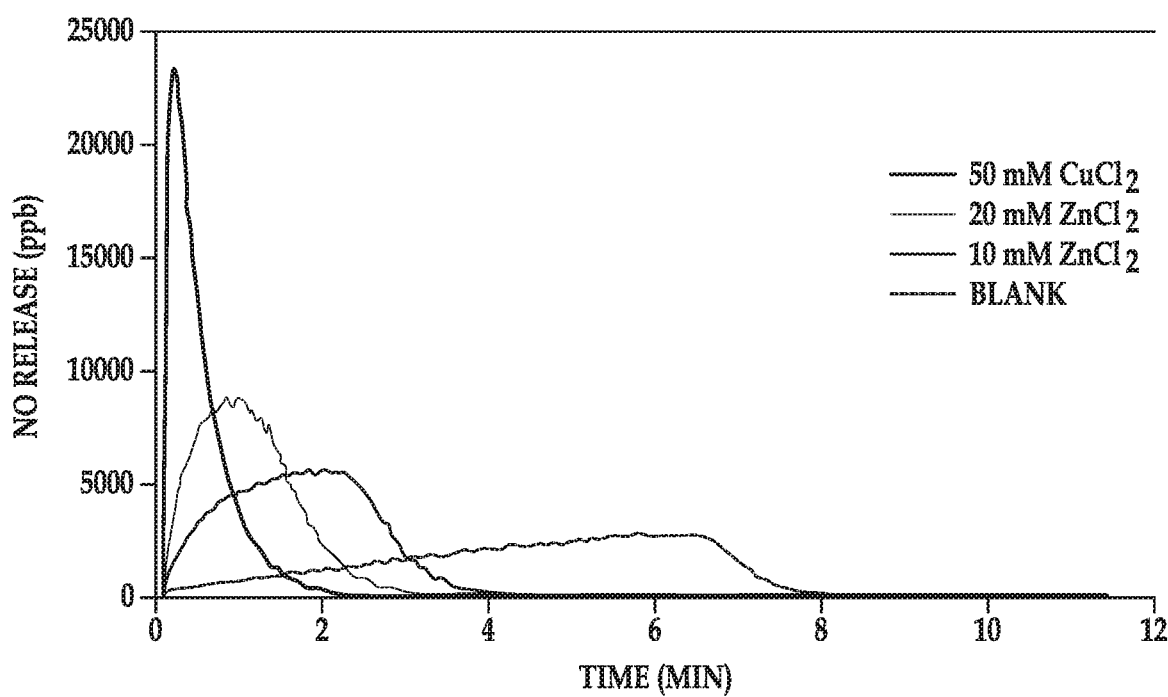
FIGS. 2A and 2B are graphs depicting nitric oxide (NO) release plots of S-nitroso-n-acetylpenicillamine (SNAP) injections into a nitric oxide analyzer, where
Figure 2B:
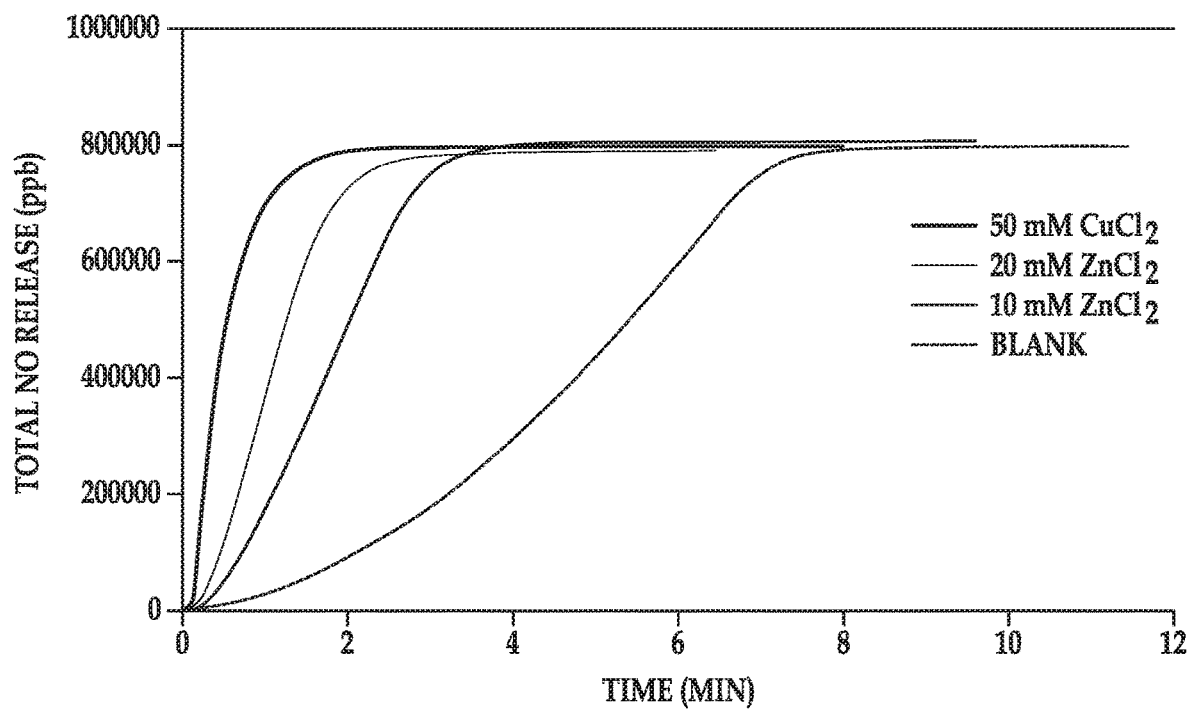

Potential of ZnO in NO Release/Promotion 3.5 mg of SNAP were dissolved in 4 mL PBS (phosphate buffered saline) with 100 mM EDTA (ethylenediaminetetraacetic acid). 25 μL of this aqueous SNAP solution was injected into a reaction cell containing 4970 μL PBS (no EDTA) and 30 μL of a sample metal ion (i.e., 10 mM $ZnCl_2$, 30 mM $ZnCl_2$, or 50 mM $CuCl_2$). A blank or control sample was also injected, and the blank did not include any metal ions. The nitric oxide was detected using an NO analyzer operatively connected to the reaction cell. The NO plots of each injection are shown in FIGS. 2A and 2B. As shown in each of these figures, the presence of transition metals clearly promotes NO release from SNAP, and zinc is shown to have NO-release properties similar to copper.

Figure 3A:
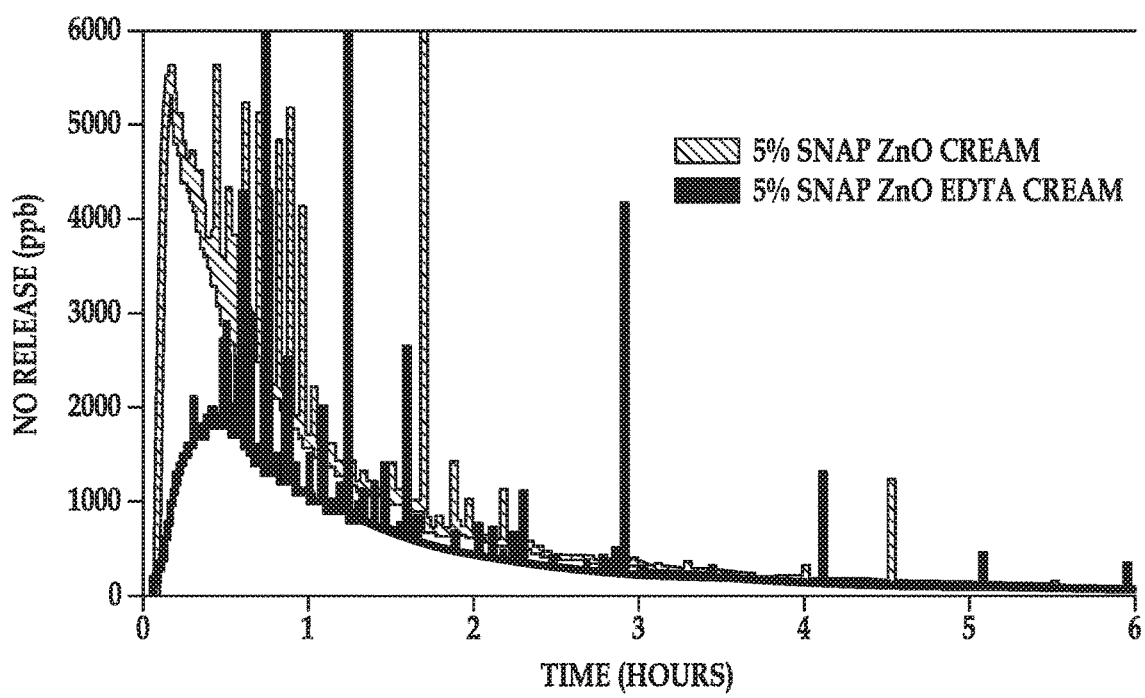
FIGS. 3A and 3B are graphs depicting NO release plots of S-nitroso-n-acetylpenicillamine (SNAP) in zinc oxide cream, where
Figure 3B:
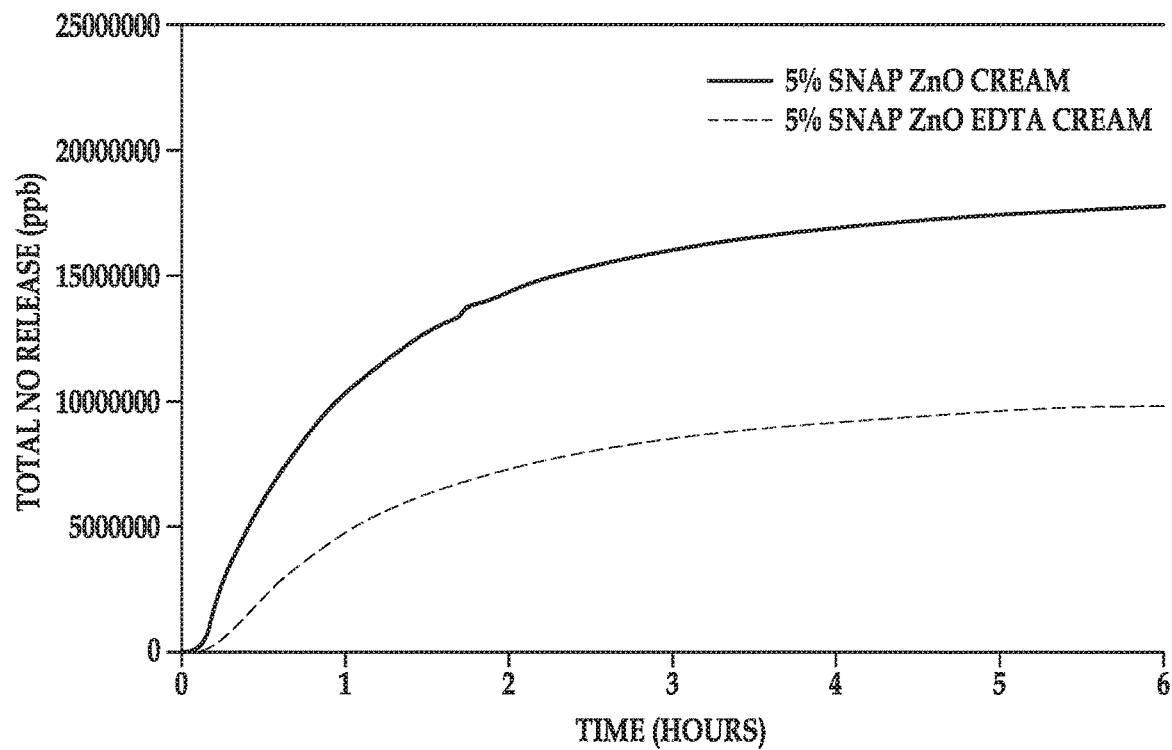

To confirm the potential of zinc, 5 wt % of SNAP was added to zinc oxide cream. In a comparative formulation, EDTA was added to neutralize free zinc ions that were predicted to initiate NO release. The mixtures were applied to glass slides and NO release was analyzed via chemiluminescence. The chemiluminescence results are shown in FIGS. 3A and 3B. Without the presence of EDTA, the zinc cream showed 70% more NO release over a six-hour period, confirming the potential of zinc creams as an NO-releasing initiator.

To determine if zinc ions ($Zn^{2+}$) can release NO from GSNO, a nitric oxide (chemiluminescence) analyzer was used to monitor the NO release profile. A bulk solution was prepared including 1 mM GSNO in an electrolyte solution (150 mM NaCl and 2.5 mM KCl). The bulk solution was purged with nitrogen gas throughout the experiment. Then, 1 mL of electrolyte solution (containing no zinc ions) was injected into the vessel. Next, the experiment was repeated using fresh 1 mM GSNO solution as the bulk solution. This time, 1 mL of 1 mM zinc chloride ($ZnCl_2$) solution in electrolyte solution was injected into the bulk solution. Comparing the two injections, it was observed that very little NO was released over a short duration for both injections. This data (not shown) suggested that zinc ions were not responsible for the prolonged NO release observed with ZnO.

Figure 3C:
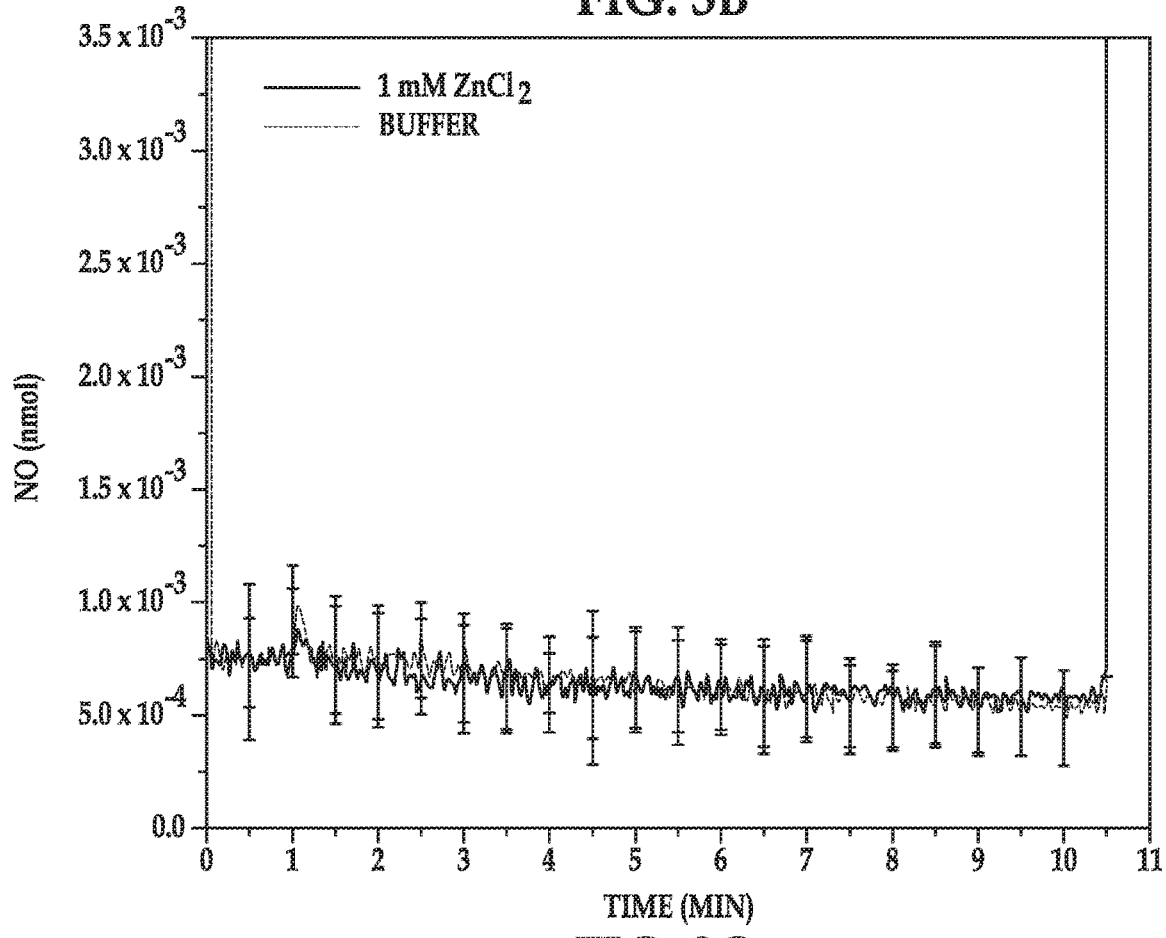
FIG. 3C is a graph depicting real-time NO release (nmol NO) versus time (in minutes) from a bulk solution containing 1 mM S-nitrosoglutathione (GSNO) after the addition of either 100 μL of 1 mM $ZnCl_2$ or 100 μL of a buffer at t=1 minute, and then 100 μL of 1 mM $CuCl_2$ at t=10.5 minute ($7.5 \times 10^{-4}$ nmol NO 5.5 ppb NO; data represents the mean±SEM (n=3))

Another experiment was performed to determine whether zinc ions can increase NO proliferation from GSNO in the dark at 24° C. NO release was measured using a nitric oxide (chemiluminescence) analyzer. Throughout the analysis, each solution was bubbled with $N_2$ gas at a rate of 50 mL/min. Any generated NO was carried into the analyzer by a $N_2$ sweep gas. All of the solutions were made with 10 mM Tris-HCl buffer (pH 7.4). A bulk solution was prepared including 1 mM GSNO in the buffer. 2 mL of this bulk solution were added to a sample cell and the analyzer was allowed to equilibrate for 1 minute. At t=1 minute, 100 μL of 1 mM zinc chloride ($ZnCl_2$) was added to the bulk solution. This resulted in a small, insignificant burst of NO. For the control, 100 μL of the buffer (10 mM Tris-HCl, pH 7.4) was added into the bulk solution at t=1 minute. The same insignificant burst was observed. For each scenario, at t=10.5 minutes, 100 μL of 1 mM $CuCl_2$ was added to the bulk as a positive control. A large burst in NO release was observed. The results from this experiment, shown in FIG. 3C, indicated that zinc ions do not appreciably increase NO proliferation from GSNO.

Figure 3D:
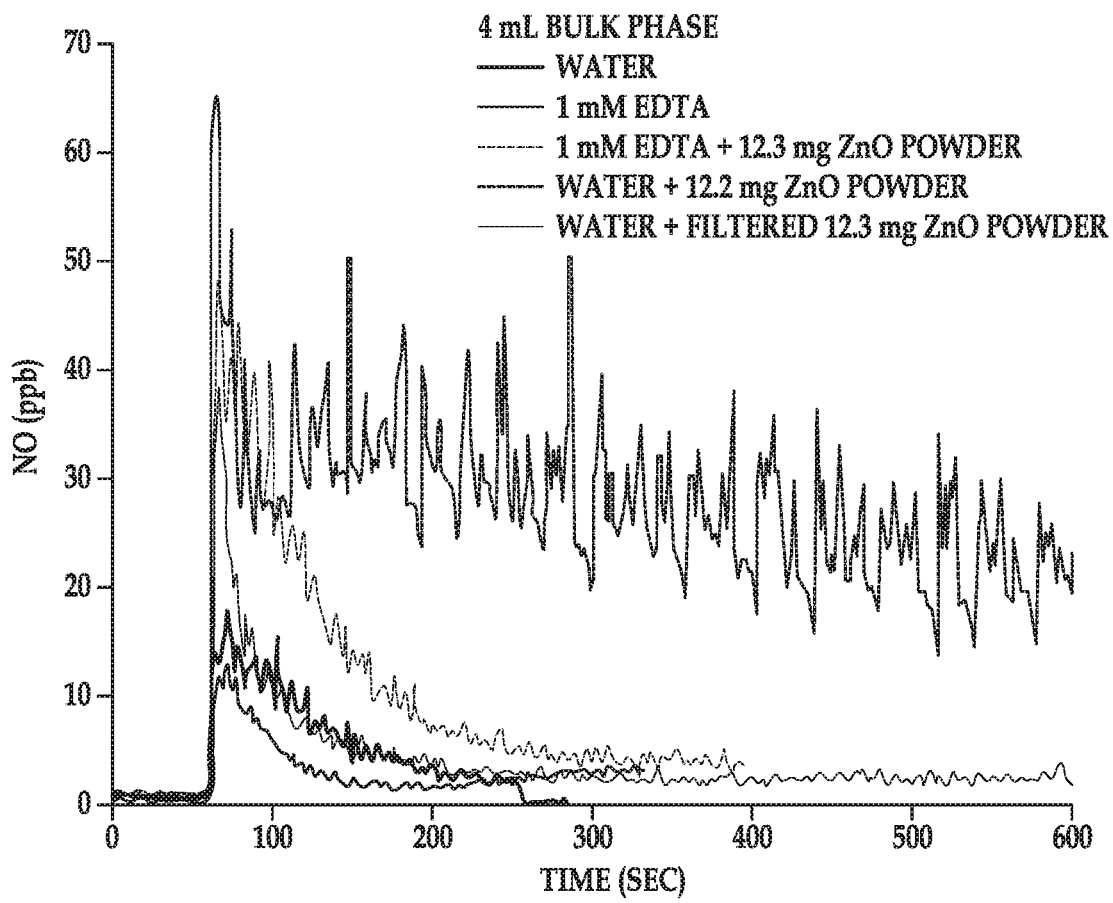
FIG. 3D is a graph depicting NO release (in ppb) over time (in seconds) of different bulk phases having 10 mM GSNO injected therein.

To determine if zinc oxide (ZnO) was capable of releasing NO from GSNO, an experiment was performed involving the injection of 10 mM GSNO into various bulk phases, including water, 1 mM EDTA, 1 mM EDTA plus 12.3 mg ZnO powder, water plus 12.2 mg ZnO powder, and water plus filtered 12.3 mg ZnO powder (each of which is identified in the key of FIG. 3D). The respective bulk solutions or heterogeneous mixtures (ZnO is not soluble in water) were purged with nitrogen gas throughout the experiments. The results are shown in FIG. 3D. As depicted, the bulk phases of water and 1 mM EDTA had no prolonged NO release after injection of 20 μL of 10 mM GSNO. The bulk phase containing 1 mM EDTA and 12.3 mg ZnO had a higher initial burst of NO upon injection of 10 mM GSNO, but no prolonged NO-release. When EDTA was not present and only ZnO was present, prolonged NO-release upon injection of 10 mM GSNO was observed. This data suggested that EDTA was hindering the ZnO from interacting with GSNO. To confirm that any trace ions present in the ZnO powder were not responsible for releasing NO from GSNO, the bulk solution of water and ZnO was filtered using a syringe filter such that any ions present would still be in the bulk solution, but the ZnO particles would not be present. No prolonged NO-release was observed when the ZnO particles were filtered out of the bulk solution.

This experiment was repeated with a bulk phase of water and 12.3 mg of ZnO powder, and by injecting 20 μL of 10 mM GSNO. After 16 hours, the base line of NO-release did not reach baseline. At this point, fresh ZnO powder was added to see if providing more ZnO surface would result in NO-release from solution. An increase in NO-release was observed upon introduction of 4.8 mg of fresh ZnO powder. These results indicated that GSNO was interacting with the surface of the ZnO particles, which weakens the SNO bond and liberates NO.

Example 2

Stability Tests

GSNO—Part I

The stability of 10 wt % GSNO in petroleum jelly was tested. The petroleum jelly used was VASELINE®.

A mixture 10 wt % GSNO in VASELINE® was mixed until homogeneity was achieved. The homogeneous mixture was spread out on a weigh boat and dried under vacuum and desiccant for 24 hours. Afterwards, individual samples were weighed out into individual amber glass vials. Each sample's mass, ranging from 15-40 mg per sample, was recorded to obtain the theoretical amount of GSNO in each sample. Septum caps were used to allow purging of each sample with nitrogen gas for storage. Each sample was purged under nitrogen gas for 5 hours. All caps were then wrapped in parafilm, and then each vial was wrapped in aluminum foil to ensure that the samples are not exposed to light. All samples were stored in the dark at room temperature (~25° C. in this example).

To quantify the amount of GSNO in each VASELINE® sample, ultraviolet-visible spectroscopy (UV-Vis) was used. GSNO has strong absorption at 344 nm, rising from a $\pi \rightarrow \pi^*$ transition. After recording the absorption of a sample, Beer's law (A=εbc, where A=absorption, ε=922 $M^{-1}$ $cm^{-1}$, b=1 cm, and c=concentration) was used to calculate the concentration of GSNO. These measurements were made at different times over several months.

When a stored GSNO/VASELINE® sample was going to be analyzed, it was opened, subjected to 5 mL of xylene, vortexed for 30 seconds, and stirred for 10 minutes. During this process, the xylene dissolves the VASELINE®, but not the GSNO. After 10 minutes of stirring, the contents were poured into a separation funnel. The sample container was then washed twice with Milli-Q purified water and the washings were added to the separation funnel. The separation funnel was then gently shaken for 1 minute. Any GSNO that was in the sample should have been dissolved in the Milli-Q water. An aliquot of the aqueous layer was taken and the absorbance spectrum was captured from 200-600 nm using UV-Vis to quantitate the level of GSNO present in the GSNO/VASELINE® sample.

Figure 4A:
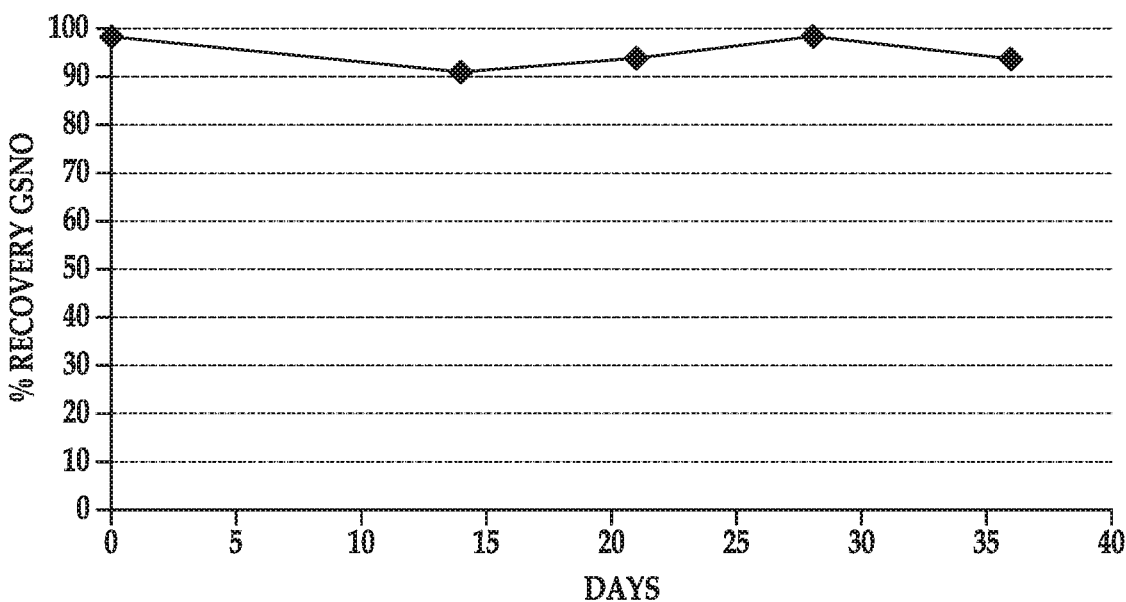
FIG. 4A is a graph depicting the % Recovery over time (in days) of S-nitrosoglutathione (GSNO) from a 10 wt % GSNO in VASELINE® sample after being stored for 36 days at room temperature and in the dark.

FIG. 4A illustrates the storage stability results over a 36-day period. In particular, FIG. 4A shows the % Recovery of GSNO from the 10 wt % GSNO in VASELINE® samples over the 36-day period. These results show that GSNO is rather stable in VASELINE® for 36 days (just over 1 month) at the specified storage conditions.

The stability of the 10 wt % GSNO in VASELINE® samples continued to be monitored, and the samples were again tested after 67 days of storage (just over 2 months). While not shown, the results indicated that the GSNO was still stable in the VASELINE® after 67 days of storage at the specific conditions.

The stability of the 10 wt % GSNO in VASELINE® samples continued to be monitored, and the samples were again tested just over 3 months of storage and again just over 5 months of storage. While not shown, the results at 3 and 5 months indicated that the GSNO was still stable in the VASELINE® at the specific conditions. At the +5 month period, there was no measureable loss of GSNO levels in the mixtures when stored at the specified conditions.

GSNO—Part II

Two different concentrations, 10 wt % and 33 wt %, of GSNO in VASELINE® were prepared to evaluate the long-term stability of GSNO in VASELINE® at 24° C., in the dark, and in dry storage (under $N_2$ gas).

The preparation of each sample was completed in the absence of direct light. A mortar and pestle were used to grind GSNO crystals into a fine powder. The desired mass of fine GSNO powder was then weighed out into a mixing vessel. In the same vessel, the desired mass of VASELINE® was added. The fine GSNO powder was then mixed thoroughly with the VASELINE® using a wooden stirrer for about 2.5 minutes.

The samples were respectively placed into 20 mL amber glass vials with septum caps and were wrapped in aluminum foil. The vials were purged with nitrogen gas via the septum top for about 5 hours. The samples were then stored in the dark at 24° C. for extended time periods. Dark storage was used to avoid photochemical decomposition of GSNO.

UV-Vis spectroscopy was used to determine the stability of GSNO in VASELINE®. Sample prep for UV-Vis was performed as described in Part I of this Example. After sample prep, the aliquot of the aqueous layer was taken in an appropriate volume so that the absorbance measured would be <1 at 334 nm. The sample was further diluted if necessary to achieve an absorbance of <1. The spectra were obtained by scanning from 300-500 nm at a scanning speed of 240 nm/min. Milli-Q purified water was used as the blank to standardize the baseline absorbance.

Figure 4B:
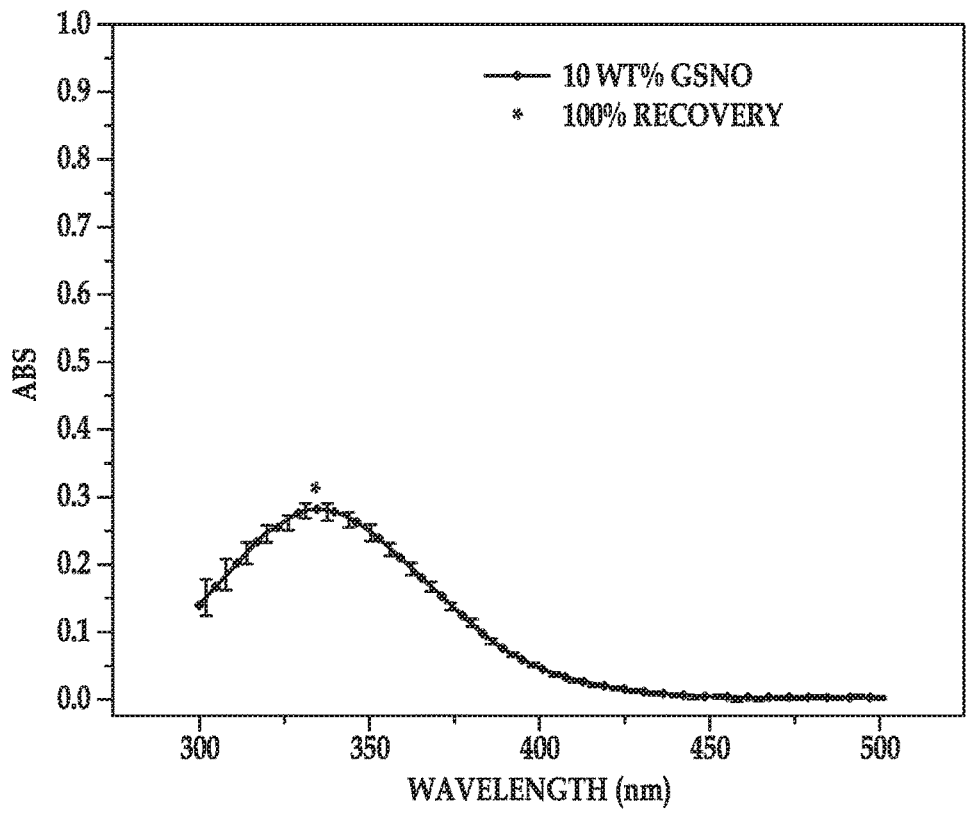
FIG. 4B is a graph depicting the Absorbance (ABS) versus wavelength (nm) for a 10 wt % GSNO in VASELINE® sample after being stored for 583 days at room temperature and in the dark (data represents the mean±SEM (n=3))
Figure 4C:
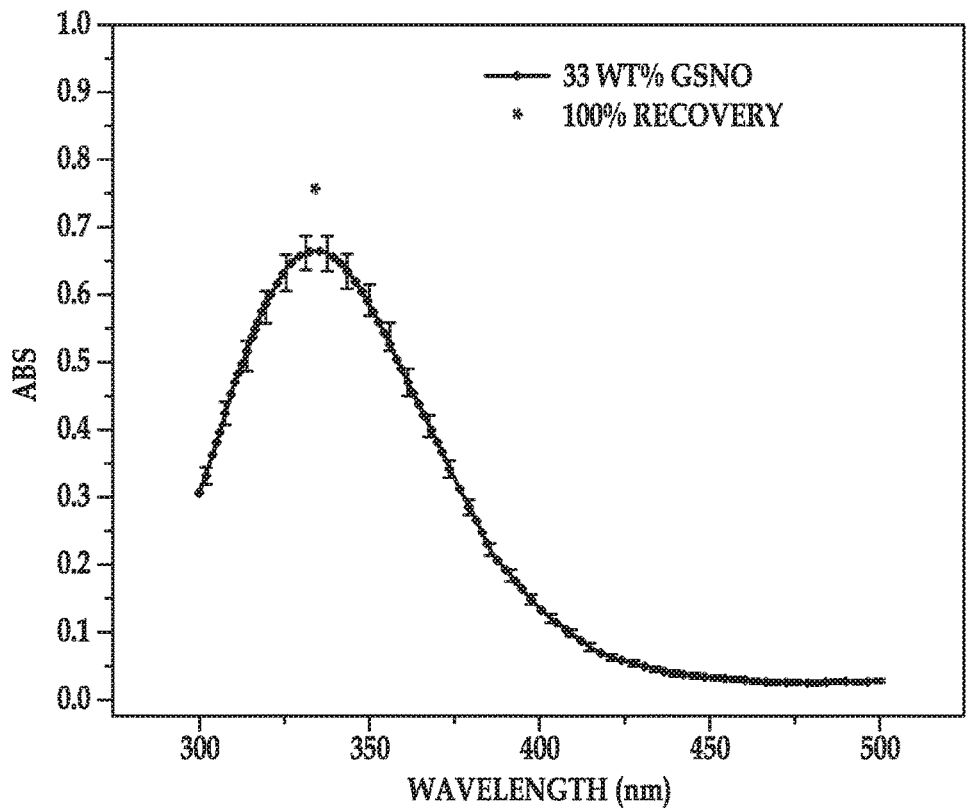
FIG. 4C is a graph depicting the Absorbance (ABS) versus wavelength (nm) for a 33 wt % GSNO in VASELINE® sample after being stored for 313 days at room temperature and in the dark (data represents the mean±SEM (n=3))

Absorbance (ABS) versus wavelength (nm) was measured for both the 10 wt % and 33 wt % GSNO in VASELINE® samples on day 583 and day 313, respectively. The results are shown in FIG. 4B for the 10 wt % sample and in FIG. 4C for the 33 wt % sample. In each of FIGS. 4B and 4C, the star represents the theoretical ABS value at 334 nm for 100% recovery of GSNO. The theoretical ABS value for each of the GSNO samples was calculated using Beer's law and an extinction coefficient of $\varepsilon_{334\,nm}=922$ $M^{-1}$ $cm^{-1}$ for the GSNO. The absorbance at 334 nm was then used to calculate the % Recovery of GSNO from the stored samples. The % Recovery for the 10 wt % GSNO in VASELINE® sample on day 583 was 89.8±3.4%. The % Recovery for the 33 wt % GSNO in VASELINE® on day 313 was 87.6±3.5%. The longevity of GSNO stability at 24° C. suggests that the dry GSNO sequestered within the viscous VASELINE® matrix may increase GSNO's thermal stability due to favorable geminate recombination of the thiyl and NO radical pair. It is believed that any of the examples of the first composition disclosed herein including GSNO may be stored at room temperature or colder temperatures for up to 2 years.

SNAP

The stability of 5 wt % and 10 wt % SNAP in petroleum jelly was tested. The petroleum jelly used was VASELINE®.

Mixtures of 5 wt % SNAP powder or 10 wt % SNAP powder in VASELINE® were mixed until homogeneity was achieved. Each homogeneous mixture was spread out on a weigh boat and dried under vacuum and desiccant for 24 hours. Afterwards, individual samples were weighed out into individual amber glass vials. Each sample's mass was recorded to obtain the theoretical amount of SNAP in each sample. Septum caps were used to allow purging of each sample with nitrogen gas for storage. All caps were then wrapped in parafilm, and then each vial was wrapped in aluminum foil to ensure that the samples are not exposed to light. All samples were stored in the dark at room temperature (~25° C. in this example).

To quantify the amount of SNAP in each VASELINE® sample, UV-Vis was used. After recording the absorption of a sample, Beer's law (A=εbc, where A=absorption, ε=922 $M^{-1}$ $cm^{-1}$, b=1 cm, and c=concentration) was used to calculate the concentration of SNAP. These measurements were made at different times over several months.

When a stored SNAP/VASELINE® sample was going to be analyzed, it was opened and 40 mg of the sample was retrieved. The 40 mg sample was dissolved in 4 mL of a solution including a 1:2 weight ratio of dimethyl acetamide (DMAc) and chloroform ($CHCl_3$) to respectively dissolve the SNAP and the VASELINE®. During this process, the DMAc dissolves the SNAP and the $CHCl_3$ dissolves the VASELINE®. The SNAP solution was diluted 1:10 twice, and used to obtain UV-Vis absorbance values between 0.2 and 2 AU (absorbance units) at $\pi_{max}$.

At about 1.5 months, the 5% SNAP in VASELINE® sample exhibited a % Recovery of 83.2%, and the 10% SNAP in VASELINE® sample exhibited a % Recovery of 107.9%. The greater than possible yield for the 10% sample may have been due to the mixture having been non-uniform. At just over 5 months, the 5% SNAP in VASELINE® sample exhibited a % Recovery of 91.4%. These results indicate that SNAP is relatively stable in VASELINE®.

5% SNAP, 10% SNAP, and 33% SNAP in VASELINE® samples prepared as previously described were also stored at room temperature (~25° C.) in a covered box, which was then placed in a drawer. Samples were recovered and dissolved as previously described and measure via UV-Vis (at $\lambda_{max}=342$ nm). The results are shown in Table 1. Table 1 also shows a control of 100% SNAP powder, which was also stored under the same conditions.

TABLE 1

| Sample | Storage Period | % Recovery |
|---|---|---|
| 100% SNAP powder | 156 days | 94.3 |
| 5% SNAP/VASELINE ® | 541 days | 74.6 |
| 10% SNAP/VASELINE ® | 168 days | 97.0 |
| 33% SNAP/VASELINE ® | 118 days | 92.5 |

These results also indicate that SNAP is relatively stable in VASELINE®.

Example 3

NO Release Tests

Comparison of GSNO and Sodium Ascorbate (NaAsc) Versus GSNO and Zinc Oxide

A comparative composition (GSNO with equal moles of NaAsc in VASELINE® mixed with NEOSPORIN®) was prepared as follows. A mixture of 10 wt % GSNO in VASELINE® with equal moles of NaAsc was prepared. This mixture was mixed at a weight ratio of 50:50 with the commercially available cream NEOSPORIN® (which does not contain zinc oxide). The resulting mixture provided a 5 wt % GSNO cream with equal moles of NaAsc.

An example composition (GSNO in VASELINE® mixed with 13% ZnO cream) was prepared as follows. VASELINE® containing 10 wt % GSNO was prepared. This mixture was then mixed at a 50:50 weight ratio with a commercially available ZnO cream. The resulting 50:50 mixture provided a final concentration of 5 wt % GSNO and 6.5% ZnO within the mixture.

Thin films (0.41 mm) were formed with each of the comparative composition and the example composition, and NO release was analyzed. The NO release profiles for the comparative thin film and the example thin film are shown in FIG. 5A, and the moles of NO released versus time for the comparative thin film and the example thin film are shown in FIG. 5B.

Figure 5A:
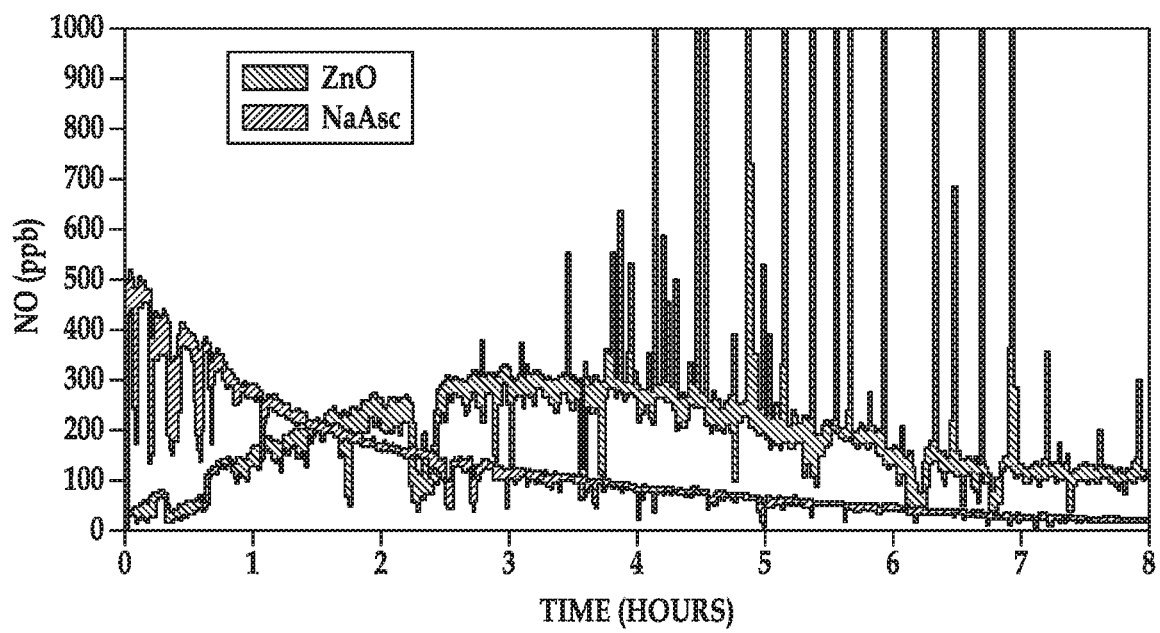
FIG. 5A is a graph depicting NO release profiles (in ppb) over an 8 hour period for a comparative thin film (GSNO and ascorbate in VASELINE® and NEOSPORIN®) and for an example thin film (GSNO in VASELINE® and ZnO mixture)
Figure 5B:
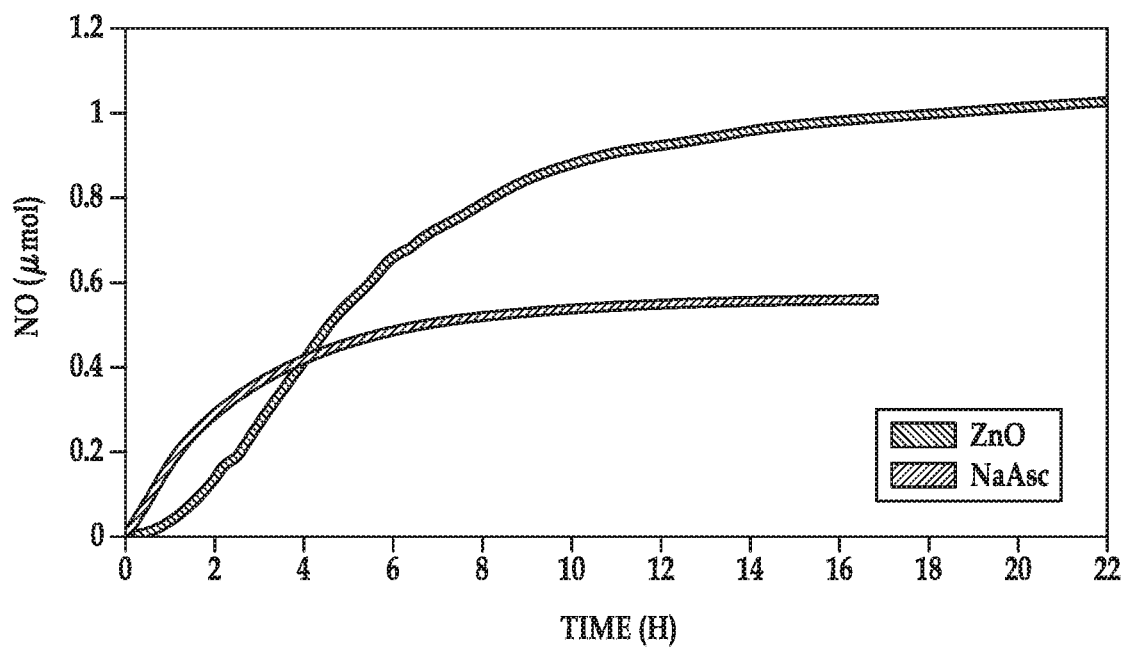
FIG. 5B is a graph depicting the moles (μmol) of NO released versus time (in hours) for the comparative and example thin films described in FIG. 5A.

As shown in FIG. 5A, the NO-release study of the comparative thin film revealed that the amount of NO released from this mixture was between 40% and 60% of the total GSNO present. The NO-release profile for the comparative thin film showed a large burst at the beginning with steady decrease over time (FIG. 5A). The majority of NO was released within the first 6 hours. After 6 hours, the same number of moles of NaAsc was added to the sample. At this point, there was a slight increase in NO detection, which confirms that NaAsc is not a catalyst and that the initial amount of NaAsc present in the cream is not fully reacting with the GSNO. Indeed, some of the NaAsc is likely decomposing (being oxidized) before reacting with the GSNO, and this limits the amount of NO that can be emitted from the comparative thin film.

As shown in FIG. 5A, the NO-release study using the example thin film revealed that the amount of NO released was approximately 82% of the total GSNO present. The NO-release profile revealed a trend that was not observed using NaAsc. Indeed, there is no initial burst of NO release at the beginning, but a rather a more gradual increase of NO-release (FIG. 5A). As shown in FIG. 5B, the NO was continuously released for 22 hours (data only up to 8 hours shown in FIG. 5A). The large bursts observed (that appear like noise in FIG. 5A) can be attributed to tiny NO bubbles forming under the surface of the Vaseline/ZnO cream thin film and then bursting to release larger amounts of NO.

Comparison of SNAP and Sodium Ascorbate (NaAsc) Versus SNAP and Zinc Oxide

A comparative composition (SNAP with equal moles of NaAsc in VASELINE® mixed with a commercial 13% ZnO cream) was prepared as follows. A mixture of 10 wt % SNAP in VASELINE® was mixed with the ZnO cream in a 50:50 mix, and equal moles of NaAsc was added. The resulting mixture provided a 5 wt % SNAP cream with equal moles of NaAsc.

A second comparative composition (SNAP in VASELINE® mixed with NEOSPORIN®) was prepared as follows. A mixture of 10 wt % SNAP in VASELINE® was mixed with the NEOSPORIN® in a 50:50 mix. The resulting mixture provided a 5 wt % SNAP cream.

An example composition (SNAP in VASELINE® mixed with 13% ZnO cream) was prepared as follows. VASELINE® containing 10 wt % SNAP was prepared. This mixture was then mixed at a 50:50 weight ratio with a commercially available ZnO cream. The resulting 50:50 mixture provided a final concentration of 5 wt % SNAP and 6.5% ZnO within the mixture.

Thin films (0.41 mm) were formed with each of the comparative compositions and the example composition, and NO release was analyzed. The NO release profiles for the comparative thin film and the example thin film are shown in FIG. 6A, and the cumulative NO release for the comparative thin films and the example thin film are shown in FIG. 6B.

Figure 6A:
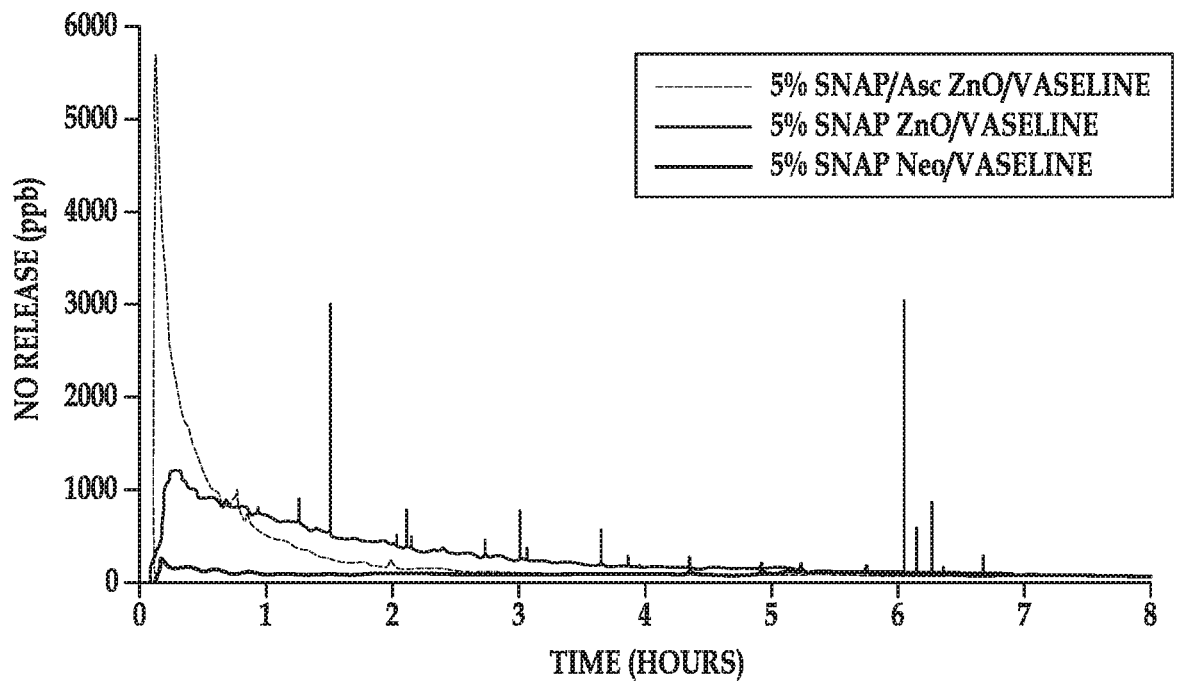
FIG. 6A is a graph depicting NO release (in ppb) over an 8 hour period for a first comparative thin film (SNAP and ascorbate in VASELINE® and ZnO), a second comparative example (SNAP in VASELINE® and NEOSPORIN®) and for an example thin film (SNAP in VASELINE® and ZnO mixture)
Figure 6B:
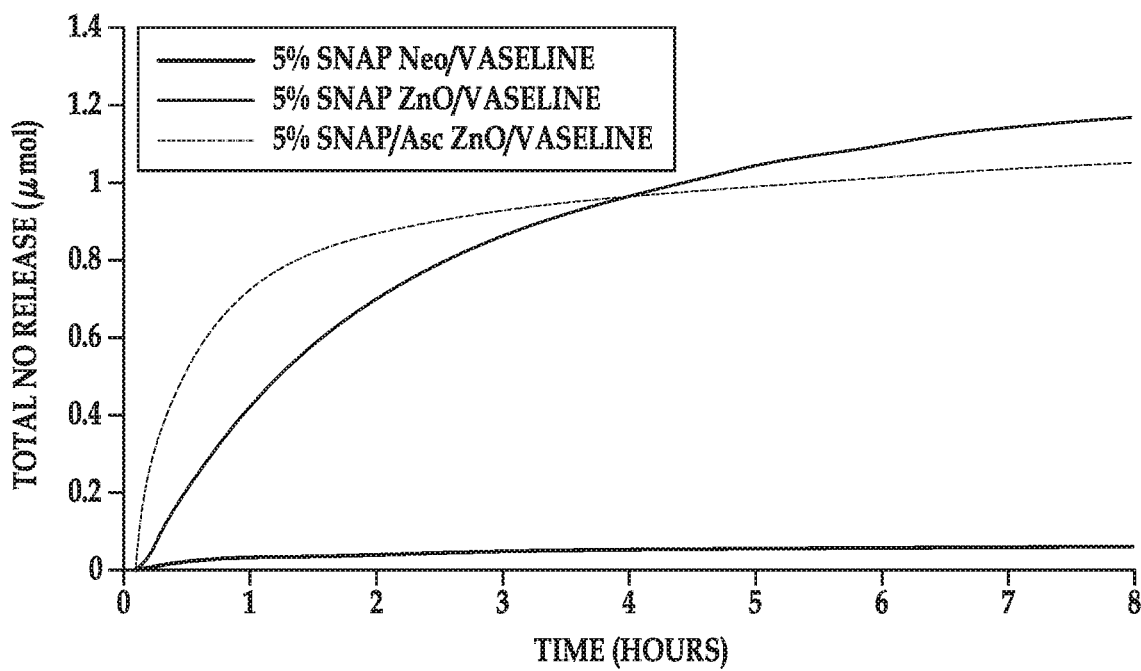
FIG. 6B is a graph depicting the cumulative NO release (in μmol) over time (in hours) for the comparative and example thin films described in FIG. 6A.

As shown in FIG. 6A, the NO release plot of the first comparative thin film (including SNAP and NaAsc) shows a very large peak in the level of NO release that then decreases significantly within the first hour. After the second hour, the first comparative thin film released NO at a very slow rate similar to the second comparative thin film (i.e., the blank cream of SNAP in VASELINE® and NEOSPORIN® with no accelerant). After 8 hours, 55% of the SNAP present in the first comparative thin film had been converted to released NO. This rapid release pattern shows potential for a fast-acting version of the NO-release topical composition disclosed herein, when the composition is mixed with ascorbate, providing two species that help accelerate the NO release from the SNAP. It was also noted that the rate of release of NO in absence of either ZnO or NaAsc was very slow (see gray line in FIG. 6A).

Also as shown in FIG. 6A, the NO release plot of the example thin film showed a peak in NO release that steadily decreased over a 6 hour period. Approximately 65% of the SNAP present in the example thin film was converted to NO over the 8 hours of testing for NO release. Again, the sudden sharp peaks observed can be attributed to NO accumulating as small bubbles within the film and bursting at different times. In FIG. 6B, it is clear that the amount of NO released was similar in both the first comparative example thin film and the example thin film, although the formulation with both NaAsc and ZnO leveled off sooner. This further suggests that ascorbate is not a catalyst for RSNOs, but its ability to hasten the rate of NO release is due to its ability to reduce SNAP to liberate the NO.

Varying Ratios of First Composition to Second Composition

GSNO in VASELINE® (first composition) was combined with ZnO cream (second composition) in this test. Sample 1 also included GSNO powder added directly to the ZnO cream with the VASELINE®. The weight percentage of GSNO was varied, as well as the weight ratio of the GSNO in VASELINE® to the ZnO cream. The NO release was measured to determine the effect of the weight ratio. Table 2 summarizes the results, in terms of total mols of NO released and the % NO released during the first 8 hour period.

TABLE 2

| Sample # | Wt % GSNO Weight Ratio of 1st comp:2nd comp | Total µmol NO/mg sample | % NO released |
|---|---|---|---|
| 1 | 3.35 wt % 0/100 | 0.0409 | 41.1 |
| 2 | 3.35 wt % 20/80 | 0.0641 | 64.4 |
| 3 | 3.35 wt % 50/50 | 0.0470 | 47.2 |
| 4 | 3.35 wt % 80/20 | 0.0170 | 17.0 |
| 5 | 6.67 wt % 50/50 | 0.0835 | 44.0 |

As expected, the formulation with the slowest and lowest NO-release has less ZnO cream (i.e., sample #4). It was observed that when incorporating GSNO powder with only the ZnO cream (i.e., sample #1), there was less NO-release compared to when GSNO was present in VASELINE® and at weight ratios of 20:80 (sample #2) and 50:50 (sample #3 and #5). It was hypothesized that during the 5 minute mixing period of the GSNO and ZnO cream, that a significant amount of the NO is proliferated from the GSNO because there was no VASELINE® present to slow the proliferation process.

Varying SNAP Concentrations in ZnO Cream

To increase the rate of NO release during the first 6 hours, the concentration of SNAP in the mixture was adjusted. Here, the concentration of the initial SNAP/VASELINE® composition was adjusted from 10 wt % to 30 wt %, resulting in a final concentration of 15 wt % SNAP in the SNAP/VASELINE® and ZnO cream mixtures.

Figure 7A:
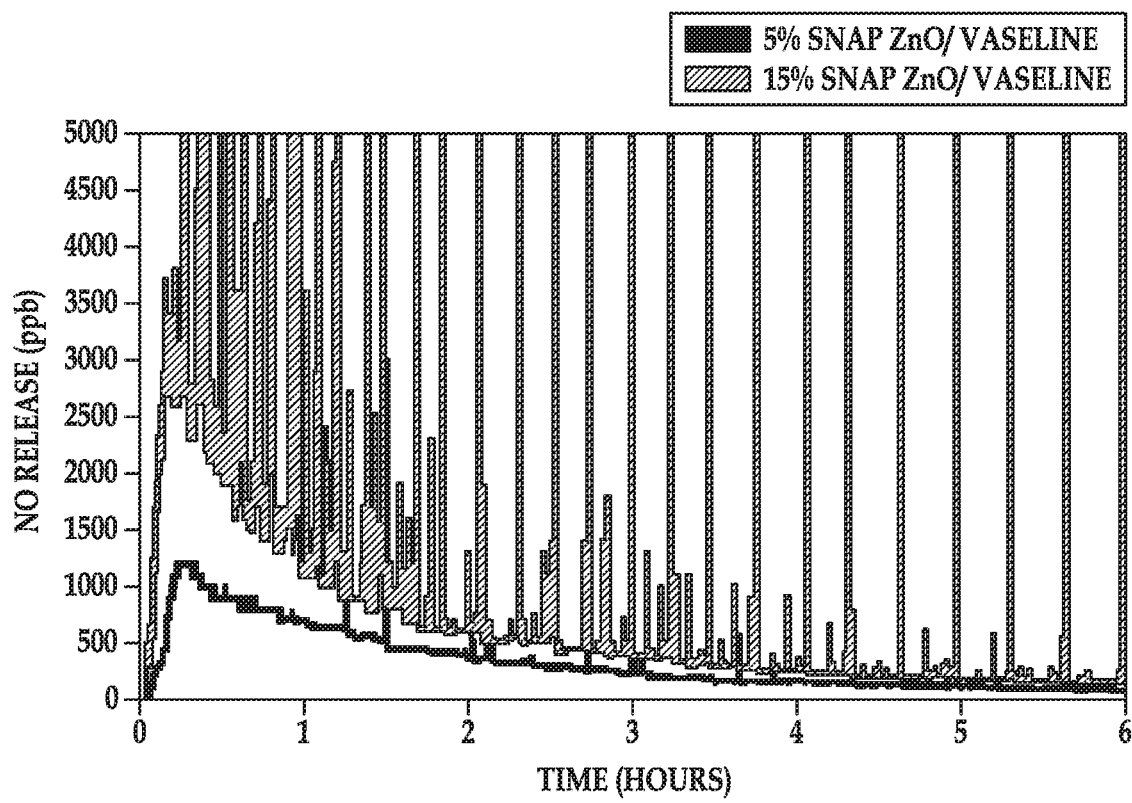
FIGS. 7A and 7B are graphs depicting NO release profiles (in ppb in FIG. 7A and as % NO release in FIG. 7B) over a 6 hour period for mixtures of ZnO cream and VASELINE® with 5% and 15% SNAP.
Figure 7B:
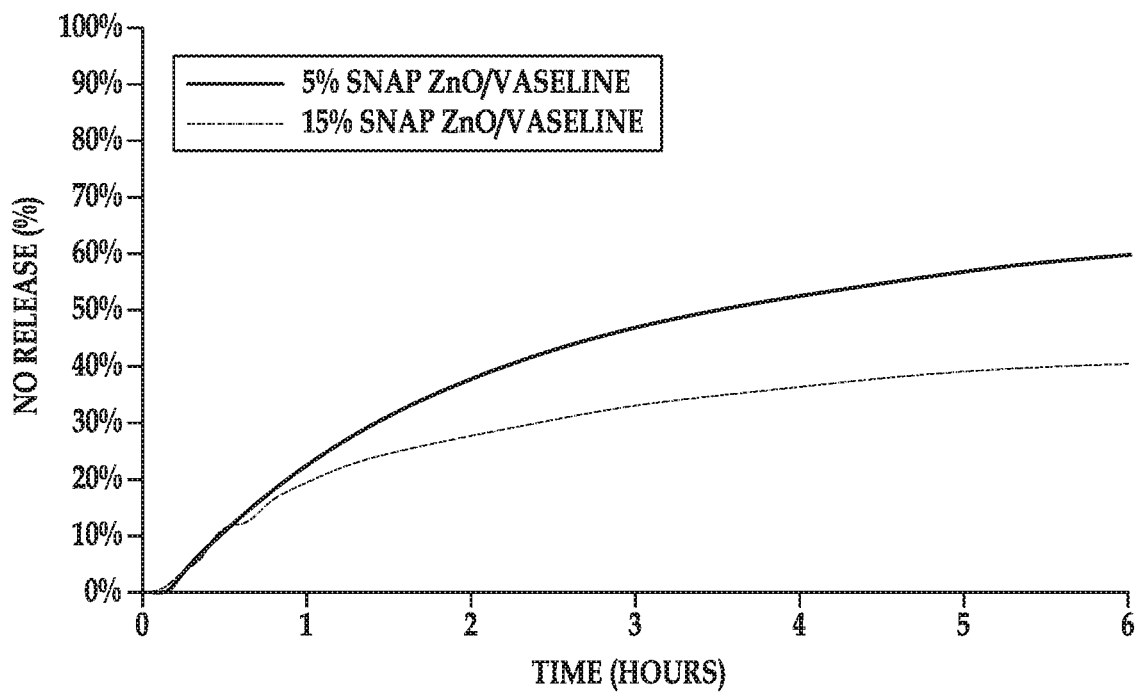

The resulting NO release profiles in FIGS. 7A and 7B show that while the rate of NO release increases (peak 1 ppm/s vs 3 ppm/s) in a more concentrated sample, the relative release in the first 6 hours will decrease. That is, the total NO release in the 15% SNAP sample increased 2.4× compared to the 5% SNAP sample, which is less than the expected 3× total release. Therefore, to increase the amount of NO release in the first 6 hours of application, it may be desirable to add an accelerant, such as ascorbate or additional zinc oxide and promote more of the SNAP to active in the initial application.

Lower SNAP concentrations (e.g., 2.5 wt %) were also tested. While not shown, the results indicated that samples with lower SNAP concentration had a stable release pattern, and may decompose the SNAP more completely than higher concentration samples.

Release with SNAP and a Catalyst

Figure 8:
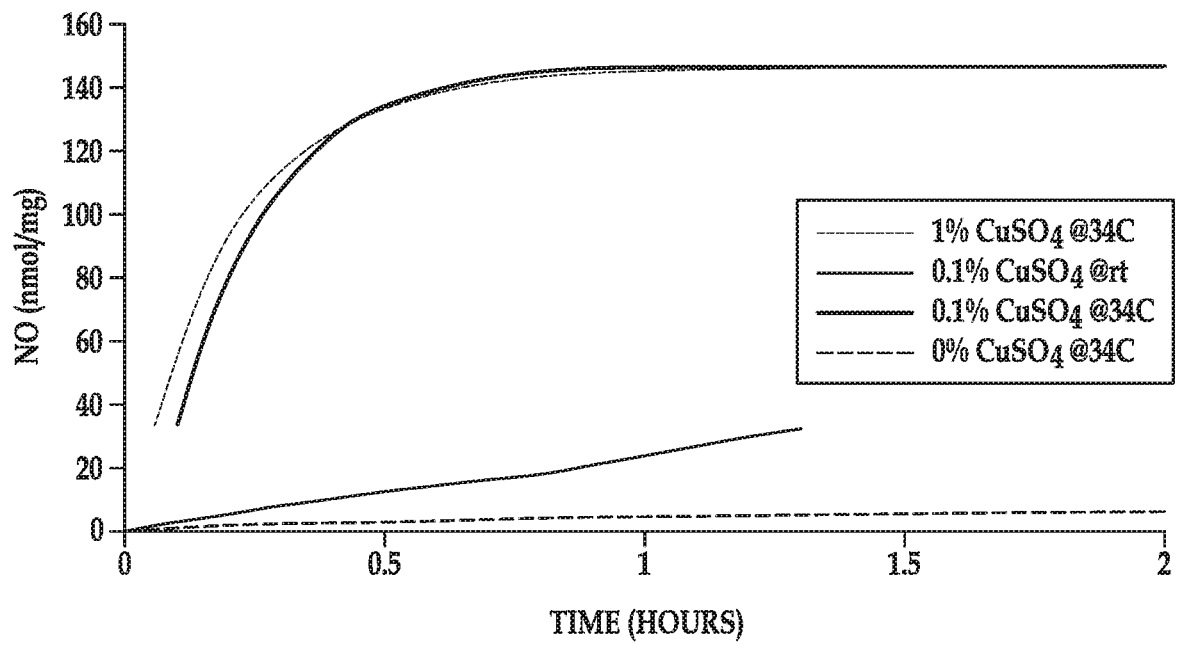
FIG. 8 is a graph depicting the NO release rates (NO, in nmol/mg versus time, in hours) from 3.3 wt % SNAP in NEOSPORIN® with different concentrations of a $CuSO_4$ catalyst.

Additional release studies were conducted with $CuSO_4$ as a catalyst for NO release from SNAP in NEOSPORIN®. The mixtures included 3.3 wt % SNAP in NEOSPORIN®, with different concentrations of the catalyst. The data in FIG. 8 suggests that $CuSO_4$ works in combination with the elevated temperature (34° C.) to promote NO release from SNAP decomposition. It is believed that this catalyst may be incorporated into the mixtures with the ZNO cream to further enhance NO release.

NO Release from Four Different Combinations

This example was performed in the absence of direct light.

A 33 wt % sample of GSNO in VASELINE® was prepared as described in Example 2.

Four different secondary matrices were selected, including DESITIN® Rapid Relief cream (referred to as zin oxide cream), NEOSPORIN®+Pain Relief cream (referred to as NEOSPORIN®), Osmotics Cosmeceuticals BLUE COPPER 5® cream (referred to as copper cream), or Avalon Organics® Intense Defense with Vitamin C Oil-Free Moisturizer (referred to as vitamin C cream). Each of these creams was weighed out on respective glass sample vials. The entire mass of the matrix plus the sample vial was measured. The samples were dried under vacuum for 7 days. On the $7^{th}$ day, the samples were re-weighed and the masses were subtracted from the original mass. The water content of each of the secondary matrices is shown in Table 3 as a weight percentage.

TABLE 3

| Matrix | Water Content (wt %) |
|---|---|
| Zinc Oxide Cream | 27.7 ± 2.2 |
| NEOSPORIN ® | 73.8 ± 0.1 |
| Copper Cream | 72.9 ± 2.5 |
| Vitamin C Cream | 71.1 ± 0.3 |

The entire procedure was completed in the absence of direct light. Respective samples of the 33 wt % sample of GSNO in VASELINE® were mixed with a desired mass of each of the secondary matrices so that the weight ratio was 27:73, yielding 9 wt % GSNO mixtures. The mixtures were stirred with a wooden stirrer for about 2.5 minutes.

NO release from the various mixtures was measured using a Sievers Chemiluminescence Nitric Oxide Analyzer (NOA) 280i (Boulder, CO). The NOA was calibrated via a two-point calibration of $N_2$ gas passed through a NOA zero air filter and a standard of 44.3 ppm NO in $N_2$ gas.

A small aliquot of each of the mixtures was placed inside of a plastic (polystyrene), circular stencil (diameter 5.85 mm, height 0.33 mm), on top of a glass slide. The excess mixture was scraped away from the top and the stencil was removed, leaving each mixture at a defined sample size. The glass slide was then place into an amber NOA sample cell. The bottom of the amber NOA sample cell was filled with Milli-Q purified water and the glass slide was placed on top of a stage above the water line such that the mixture did not come in contact with the water. The water reservoir was bubbled with $N_2$ gas at a rate of 50 mL/min to humidify the NOA sample cell to prevent the mixtures from drying out. The NO generated from the GSNO within the mixture was swept into the NOA by $N_2$ sweep gas.

After mixing, NO release was monitored over a 6 hour period. NO release for these mixtures was measured at two temperatures including room temperature (24° C.) and a temperature closer to the surface of human skin (34° C.). For measuring NO release of samples at 34° C., the amber NOA sample cell was placed in a 34° C. water bath. All amber NOA sample cells were wrapped in aluminum foil to shield the samples from light exposure.

Figure 9A:
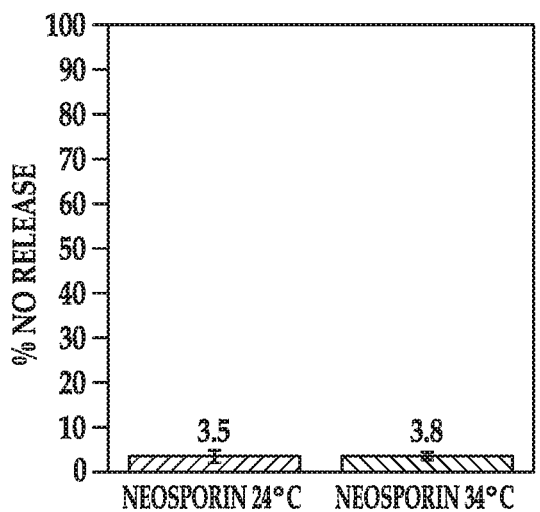
FIGS. 9A through 9D illustrate the % NO released from mixtures containing 33 wt % GSNO/VASELINE® and one of: NEOSPORIN® cream (FIG. 9A), vitamin C cream (FIG. 9B), copper cream (FIG. 9C), and zinc oxide cream (FIG. 9D) at a 27:73 weight ratio to yield 9 wt % GSNO (data represents the mean±SEM (n=3)
Figure 9B:
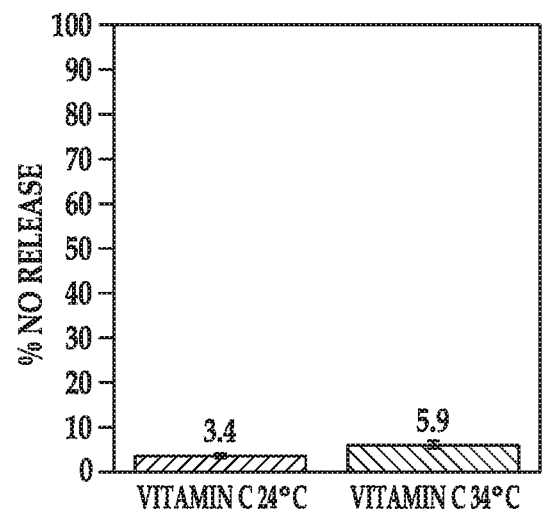
Figure 9C:
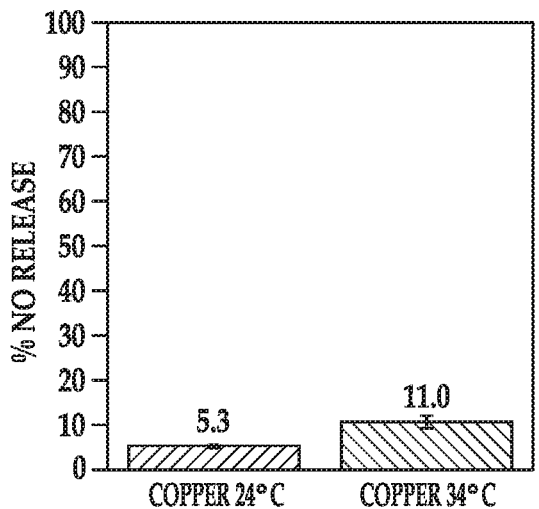
Figure 9D:
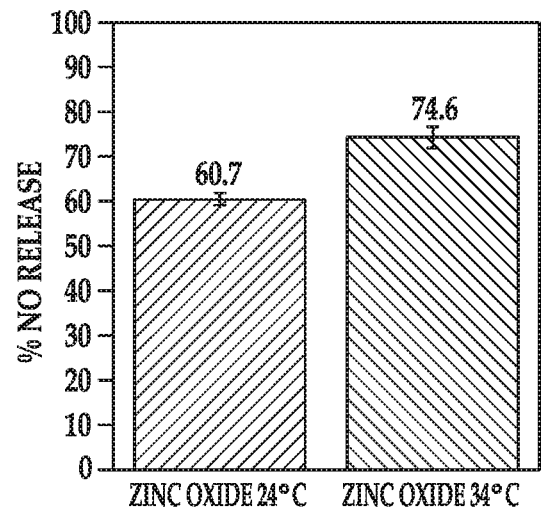

FIGS. 9A through 9D show the total % NO released from the known amount (9 wt %) of GSNO present during the 6 hour period for each secondary matrix at 24° C. and 34° C. More specifically, FIG. 9A shows the results for the mixture made with NEOSPORIN®; FIG. 9B shows the results for the mixture with vitamin C cream; FIG. 9C shows the results for the mixture with copper cream; and FIG. 9D shows the results for the mixture with the zinc oxide cream. It is clear from the data shown in FIGS. 9A through 9D that the zinc oxide cream provided a significantly enhanced rate of NO release when mixed with the GSNO/VASELINE® mixture compared to the other three creams tested.

The % NO release for both temperatures after 6 hours was extremely low for the NEOSPORIN® cream (FIG. 9A), confirming that this cream does not include any ingredients that aid in NO proliferation from GSNO. For the vitamin C cream, the active ingredient is ascorbic acid/ascorbate, which may be an accelerant for NO release. However, an extremely low % NO release was observed (FIG. 9B). The concentration of ascorbic acid in the vitamin C cream was unknown, and there may not have been enough ascorbic acid in the vitamin C cream to release an appreciable amount of NO from GSNO, because ascorbic acid is a reactant (not a catalyst) for this NO release reaction. Further, the reaction rate between GSNO and ascorbic acid may have been hindered by another molecule (e.g., tocopheryl acetate, citric acid, boric acid, tartic acid, and/or glycerine) present in the vitamin C cream.

The % NO released by the copper cream (FIG. 9C) was much lower than expected because copper ions are well-known to be a very good catalyst for NO proliferation from RSNOs. Similar to the vitamin C cream, there may have been a component in the commercial copper cream that inhibited the reaction between the copper ions and GSNO. One ingredient present in the copper cream is protocatechuic acid (PCA). PCA has shown to be a metal ion chelator as well as free radical scavenger. Therefore, the NO produced may have been scavenged, or the copper ions may have been strongly bound to PCA, not enabling them to serve as a catalyst for NO generation from GSNO.

The zinc oxide cream released significantly more NO from the GSNO/VASELINE® mixture than any other secondary matrix tested at both 24° C. and 34° C. (FIG. 9D).

Comparison of Techniques for NO Detection

Figure 10:
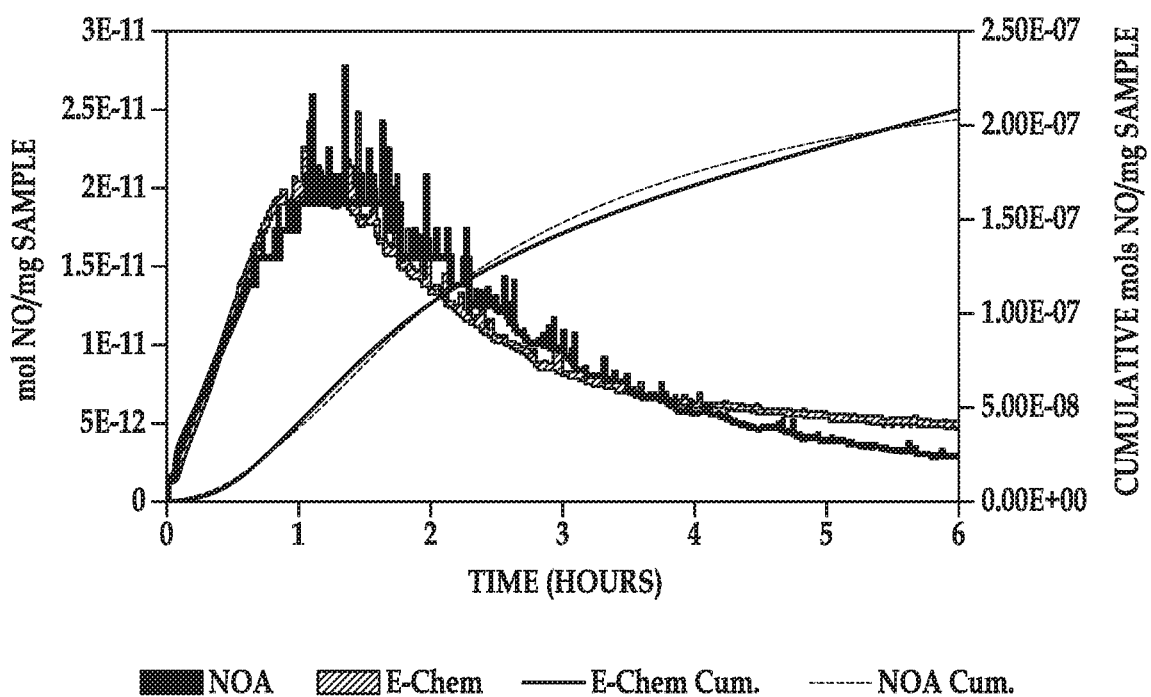
FIG. 10 is a graph depicting NO release profiles (mol NO/mg sample, left Y axis; and cumulative moles NO/mg sample, right Y axis) over time (in hours) from mixtures of ZnO cream and GSNO/VASELINE® using different analysis techniques.

To supplement the data collected via nitric oxide analyzers, NO release tests were also performed using an electrochemical (E-Chem) NO sensor system. FIG. 10 depicts the NO-release profile and cumulative NO-release of an example mixture with a final formulation of 9.1 wt % GSNO; 9.5 wt % ZnO; GSNO in VASELINE® and ZnO cream. To obtain this mixture, the GSNO in VASELINE® and ZnO cream were mixed at a weight ratio of 27.3/72.7. Quantification of NO was performed using the nitric oxide analyzer and the E-Chem NO sensor. The results shown in FIG. 10 indicate that both techniques are viable methods, and provide agreeable results. Overall, the final formulation released between 70% and 75% of the total theoretical NO present and a cumulative total of approximately 200 nmol NO/mg sample over the first 6 hour period. Both measurements were recorded under the same conditions: 34° C., humidified atmosphere, and absence of light.

NO Release Kinetics from GSNO Using Zinc Oxide

Figure 11A:
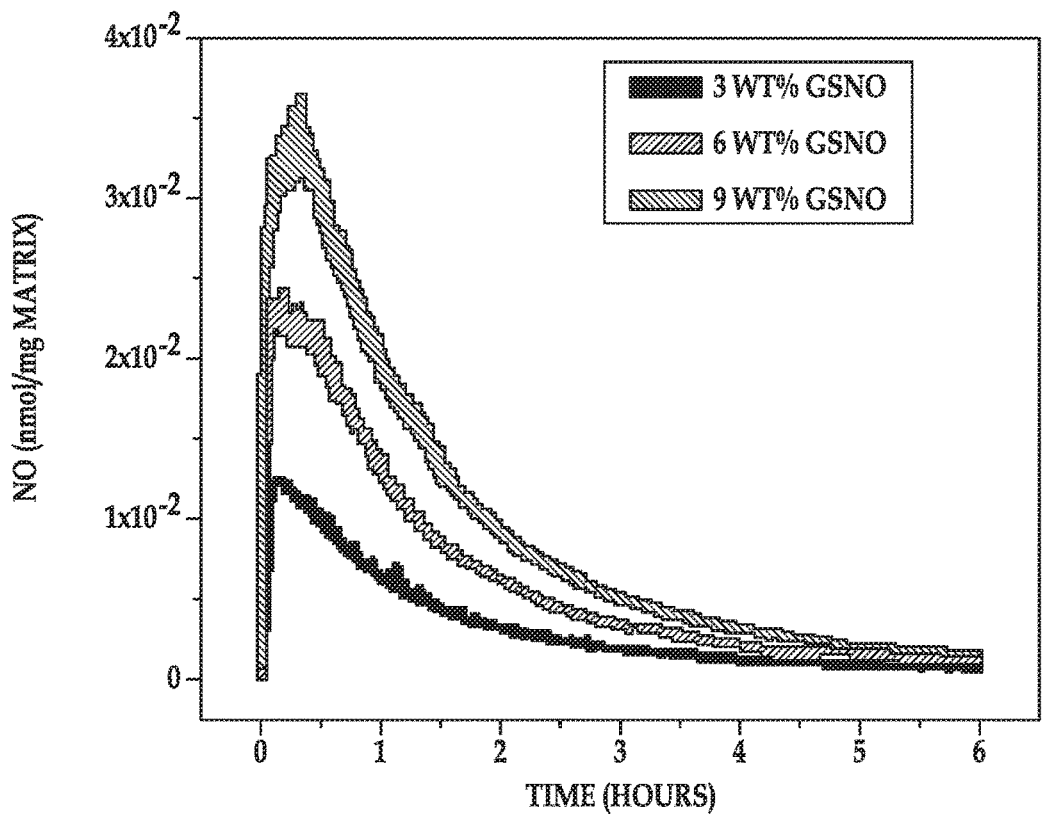
FIGS. 11A and 11B are graphs depicting nitric oxide (NO) release plots of mixtures containing zinc oxide cream and 3, 6, or 9 wt % GSNO/VASELINE®, where
Figure 11B:
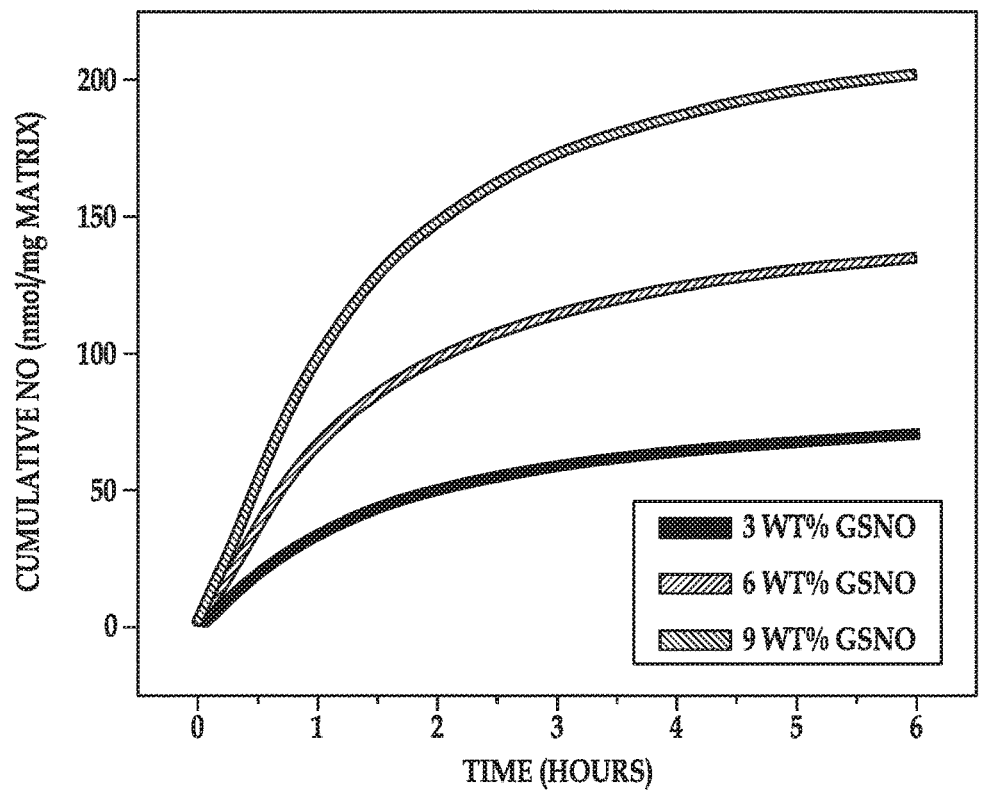
Figure 12A:
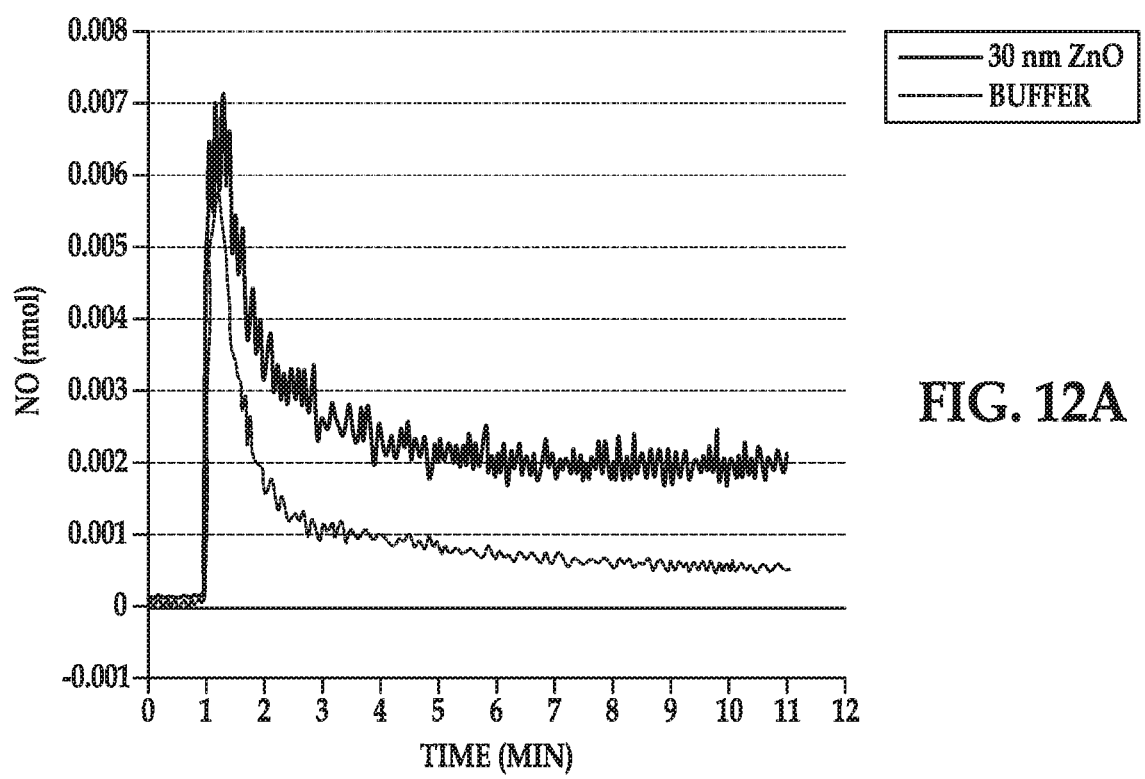
FIGS. 12A through 12E are graphs depicting real-time NO release (nmol) versus time (in minutes) after the addition of 100 μL of 10 mM GSNO into 2 mL bulk solutions containing a given component present in commercially available zinc oxide cream ($1.0 \times 10^{-3}$ nmol NO≈7.5 ppb NO; data represents the mean±SEM (n=3), error bars omitted for clarity)
Figure 12B:
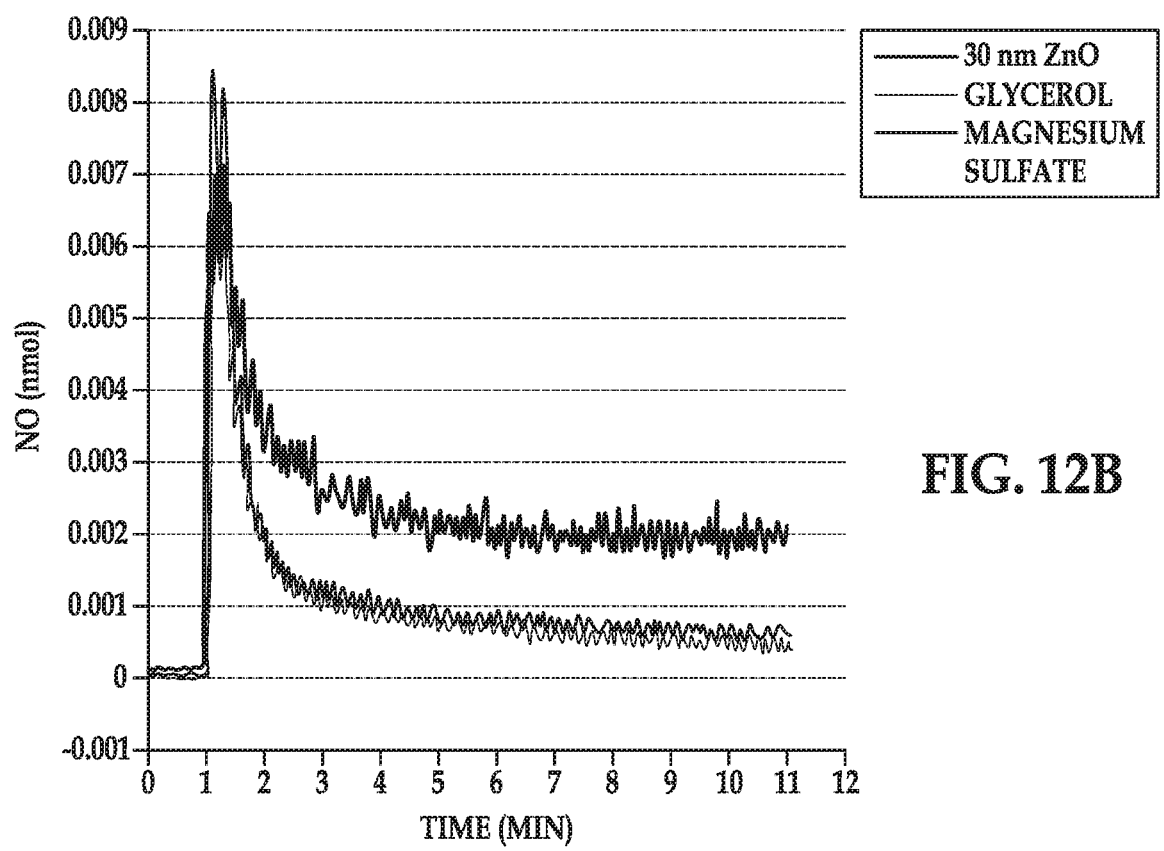
Figure 12C:
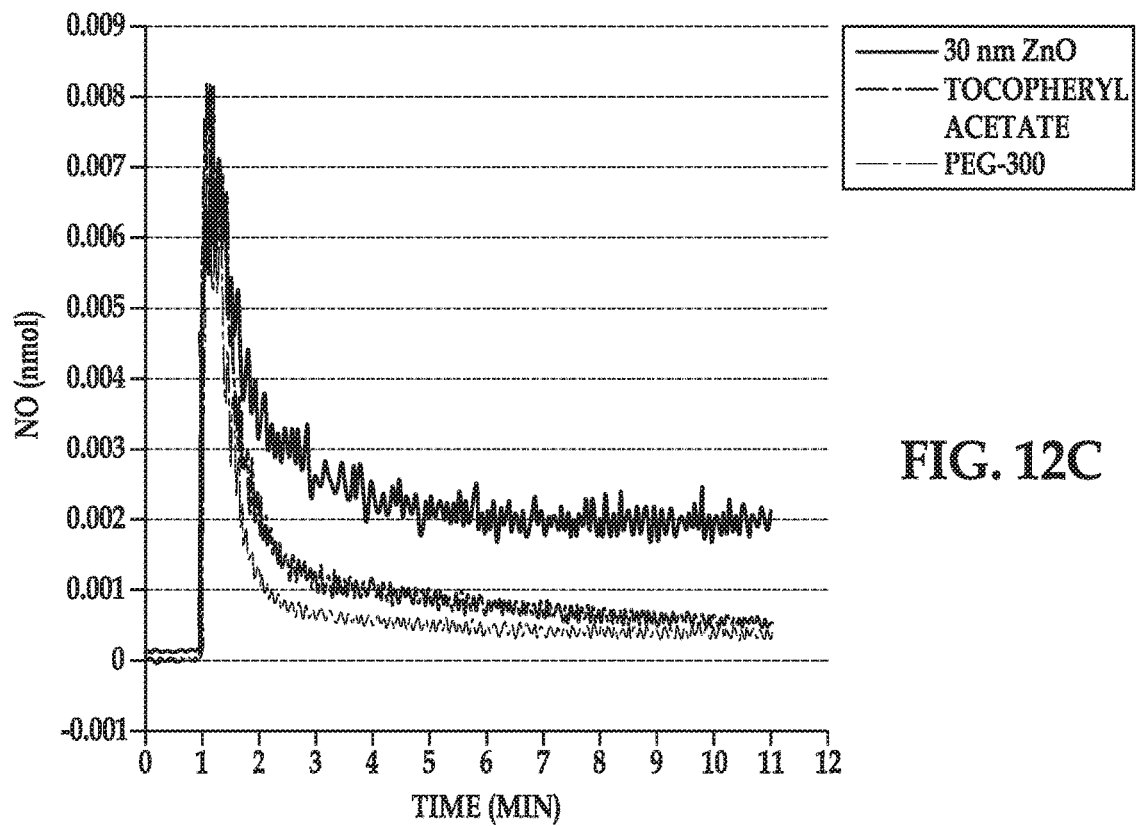
Figure 12D:
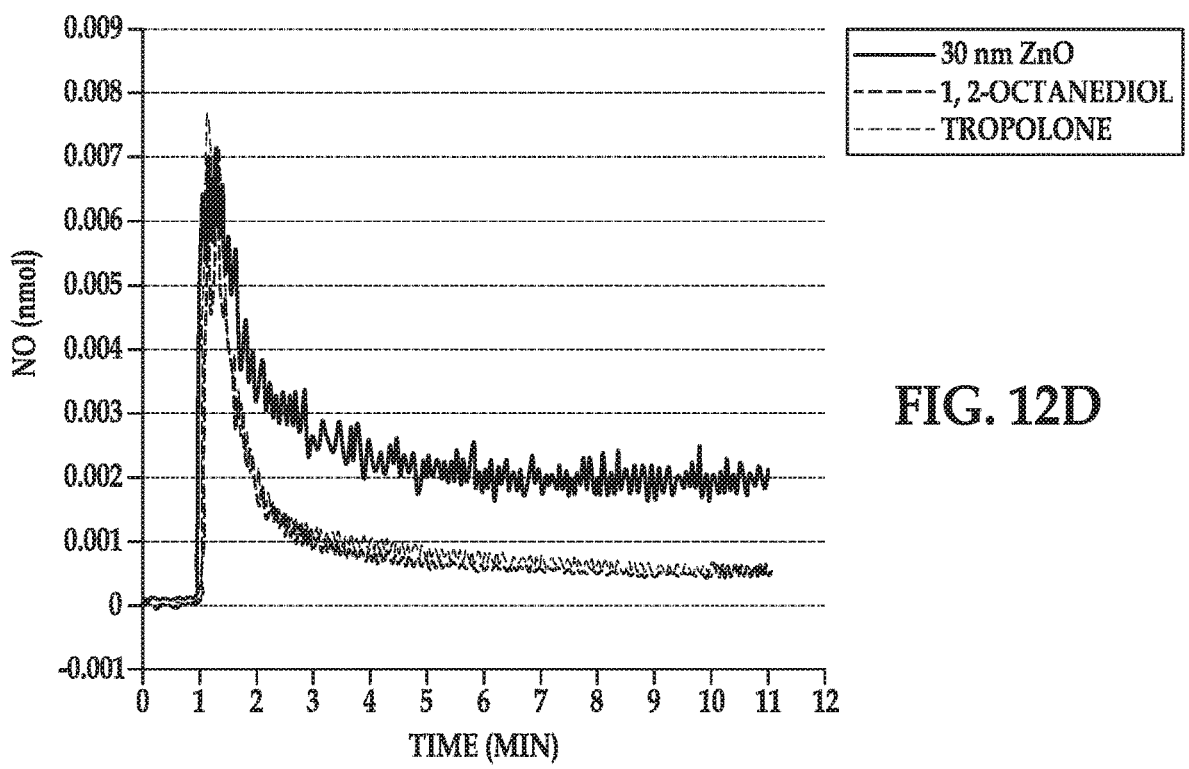
Figure 12E:
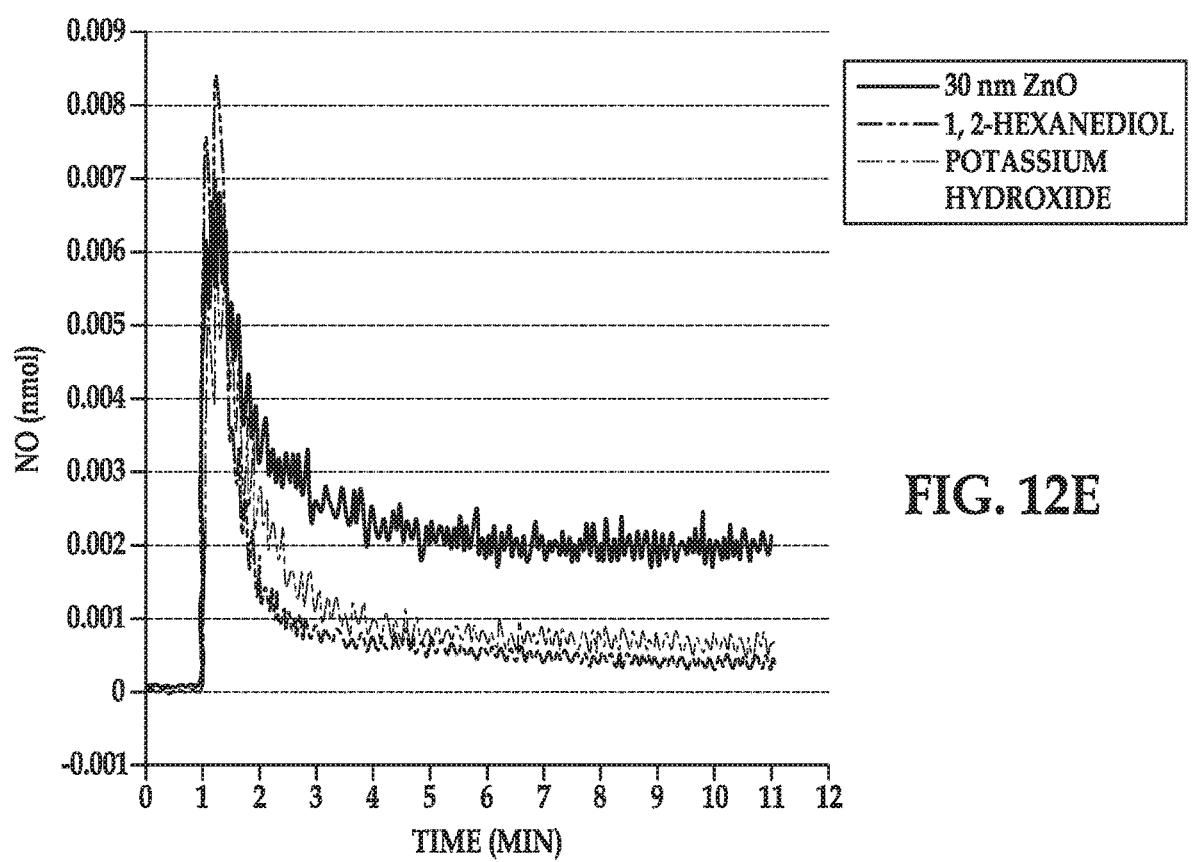

To investigate the NO release kinetics, three different concentrations of GSNO were selected. The appropriate wt % GSNO in VASELINE® mixture was mixed with the zinc oxide cream at a 27/73 weight ratio such that the final wt % of GSNO in the final mixture was 3, 6, or 9 wt %. NO release was measured at 34° C. for 6 hours, revealing that the NO release characteristics for each concentration were fairly similar (FIG. 11A). As shown in FIG. 11B, the cumulative NO release plotted versus time revealed a similar NO release trend for all three concentrations of GSNO tested, exhibiting apparent first-order kinetics.

Integration of FIG. 11A revealed that 77.9±3.8%, 75.4±3.8%, and 74.6±2.2% of the total theoretical NO available was released when employing the 3, 6, and 9 wt % GSNO final mixtures after 6 hours, respectively (Table 4). The first order rate constant ($k_{obs}$) and the half-life ($t_{1/2}$) for the 3, 6, or 9 wt % GSNO mixtures was determined by fitting the cumulative NO release versus time to a first-order rate equation. The results are shown in Table 4.

TABLE 4

| Wt % GSNO in Mixture | % NO release in 6 hours | $k_{obs}$ (h$^{-1}$) | $t_{1/2}$ (h) |
| --- | --- | --- | --- |
| 3 | 77.9 ± 3.8 | 0.58 ± 0.01 | ~1.18 |
| 6 | 75.4 ± 3.8 | 0.63 ± 0.01 | ~1.10 |
| 9 | 74.6 ± 2.2 | 0.64 ± 0.01 | ~1.08 |

While it is possible that there could be several different reactions taking place to proliferate NO from GSNO, overall the total % NO release, half-life, and rate constant values in Table 4 are very similar for all three concentrations of GSNO in the final mixtures. One minor trend that was observed was that as the concentration of GSNO increased, $k_{obs}$ increased. By increasing the concentration of GSNO, the amount of VASELINE® that was present was decreased because the mixing ratio of GSNO/VASELINE® matrix to zinc oxide cream remained the same for all three concentrations of GSNO. Therefore, as the concentration of GSNO increased, the viscosity decreased due to less VASELINE® present in the final mixtures. Decreasing the viscosity of the mixture decreased the frequency of geminate recombination between the thiyl and NO radical pair, leading to faster NO proliferation.

Example 4

Zinc Oxide Component Study

An aqueous phase test was performed to confirm that zinc oxide was responsible for NO release from GSNO. A simplified system was employed to monitor and measure NO release when GSNO was in the aqueous phase with various components/ingredients present in the commercial zinc oxide cream (DESITIN® Rapid Relief Cream: Zinc Oxide Diaper Rash Cream). Some ingredients present in the DESITIN® cream were omitted due to their low water solubility, specifically mineral oil, petrolatum, beeswax, and microcrystalline wax.

All solutions were made with 10 mM Tris-HCl buffer, pH 7.4. NO release was quantitated as described herein in the absence of light at 34° C. The components studied included 30 nm ZnO nanoparticles, glycerol, magnesium sulfate, tocopheryl acetate, PEG-300, 1,2-octanediol, 1,2-hexanediol, tropolone, and potassium hydroxide.

2 mL of buffer solution was added to amber NOA sample cells. The bulk solutions contained 10 μmol of the given test component. For each aqueous-soluble component, 5 mM bulk solutions were made in advance (e.g., glycerol, magnesium sulfate, PEG-300, 1,2-octanediol, 1,2-hexanediol, tropolone, and potassium hydroxide). For the ZnO nanoparticles, 0.82 mg were added to 2 mL of the buffer inside the amber NOA sample cell and sonicated for about 20 seconds. For testing tocopheryl acetate, 4.92 μL were added to 2 mL of the buffer inside the NOA sample cell and sonicated for about 20 seconds. The amber NOA sample cell was submerged in a 34° C. water bath and allowed to equilibrate for 1 minute. After 1 minute, 100 μL of 10 mM GSNO solution was added into the bulk solution. The final mole ratio of test component to GSNO was 10:1 μmol. The rate of NO release was monitored using the gas phase NO concentration (monitored by chemiluminescence measurements) vs. time plots.

FIGS. 12A through 12E show the NO release versus time when 100 μL of 10 mM GSNO was added into the different bulk solutions containing the given component. The data for the bulk solution containing 30 nm ZnO is repeated in each of FIGS. 12A through 12E for easy comparison of that component with the other components. When comparing the NO release profiles of all the components, only the 30 nm ZnO nanoparticles yielded significantly enhanced and prolonged NO release from GSNO. These results indicate that the pyroelectric properties of the ZnO nanoparticles may play a role in promoting proliferation of NO from GSNO in the presence of the ZnO.

Example 5

Antimicrobial Tests

LB Agar Plate Tests

In these tests, various mixtures were prepared and tested using LB agar plates and different bacteria strains (*Staphylococcus aureus* (*S. aureus*), *Pseudomonas aeruginosa* (*P. aeruginosa*), *Staphylococcus epidermidis* (*S. epidermidis*)). In these tests, a base LB agar plate was used and a 1.5 cm×1.5 cm square section of the LB agar after inoculation with a bacteria strain was placed on the base plate. To observe the effectiveness of only NO killing the bacteria (without matrix effects from the carrier), a silicone membrane (which is permeable to NO but not the carrier) was used to separate the bacteria from the mixture. The plates were incubated at 34° C. for 6 hours and then the silicone membranes (with the mixture thereon) were removed. The plates were allowed to grow overnight to visualize the killing effect on the bacteria strain and compared to the control. Control experiments had the same set up except that the mixtures were not applied.

The first mixture tested included 11.5 wt % GSNO and 4 wt % $CuSO_4$ in NEOSPORIN®; and the strains of bacteria included *Staphylococcus aureus, Staphylococcus epidermidis*, and *Pseudomonas aeruginosa*—each at a concentration of $10^5$ CFU/mL. The results for the control samples and the mixtures are shown in FIG. 10.

The second mixture tested included a GSNO in VASELINE® and ZnO cream mixture (27.3:72.7) with 9.1 wt % GSNO and 9.5 wt % ZnO; and the strains of bacteria included *Staphylococcus aureus, Staphylococcus epidermidis*, and *Pseudomonas aeruginosa*—each at a concentration of $10^5$ CFU/mL. The results for the control samples and the mixtures are shown in FIG. 11.

FIGS. 10 and 11 depict the results of the antimicrobial study with a 6 hour incubation period using the first and second mixtures previously described. Both mixtures show substantial killing effect of each strain over the 6 hour time period in which the NO-releasing mixture was applied, as compared to the respective controls. The NO-release results for the mixture used in FIG. 11 also show a slightly better killing effect than the NO-release results for the mixture used in FIG. 10.

An antimicrobial study was performed to determine the average log reduction (n=2) of each bacteria strain over time using the second mixture (i.e., the formulation including ZnO and GSNO). The method employed was as follows: overnight grown cultures (*S. aureus, S. epidermidis*, and *P. aeruginosa*) were diluted with 1×PBS buffer to about 105 CFU/ml; 50 µl of the diluted cultures were then spread onto a small LB agar plate (60 cm); ten minutes after they dried, 1.5 cm×1.5 cm squares were cut by a sterile knife and the squares were placed on top of new, small LB agar plates; NO-releasing silicone membranes or control cream membranes were placed on the top of the squares; the plates with squares were then incubated at 34° C. for 6 hours; then the membranes were removed, the squares were taken aseptically out, and 1×1 cm inner squares were cut from the initial squares to avoid edge effects; these smaller squares were then put into 15-ml corning tubes containing 1 ml of 1×PBS buffer; the PBS buffer was homogenized at full power for 30 seconds using a tissue homogenizer (OMNI TH, NW Kennesaw, Ga.); and the homogenized PBS buffer solutions were then 10-fold serially diluted with 1×PBS buffer and then the solutions were plate counted for colony enumeration. The results are shown in Table 5.

TABLE 5

| Strain | Log Reduction |
| --- | --- |
| staphylococcus aureus | 4.16 |
| pseudomonas aeruginosa | 4.04 |
| staphylococcus epidermidis | 3.10 |

Table 5 illustrates that a significant reduction in the viable counts of the three bacterial strains over 6 hours takes place when treated with the second mixture (one example of the mixture formed with the two-part topical composition disclosed herein).

The first and second mixtures described in this example were also used in a test to determine the antimicrobial effect as a function of time against *Staphylococcus epidermidis*. This test was performed as follows. Each NO release formulation (i.e., the first and second mixtures) was created and spread onto silicone thin membranes as described above (the membrane/mixture combination is referred to as a patch). Five NO-release patches were placed on top of separate LB agar squares that were previously inoculated with $10^5$ CFU/mL of *Staphylococcus epidermidis*. All samples were incubated at 34° C. in a humidified atmosphere. Each NO-release patch was then removed hourly up to the 5 hour time point. A control patch was used that did not include any NO releasing mixture. The control patch was also applied and removed after 5 hours. The plates were allowed to grow overnight to visualize the killing effect on the bacteria strain and compared to the control.

Figure 13:
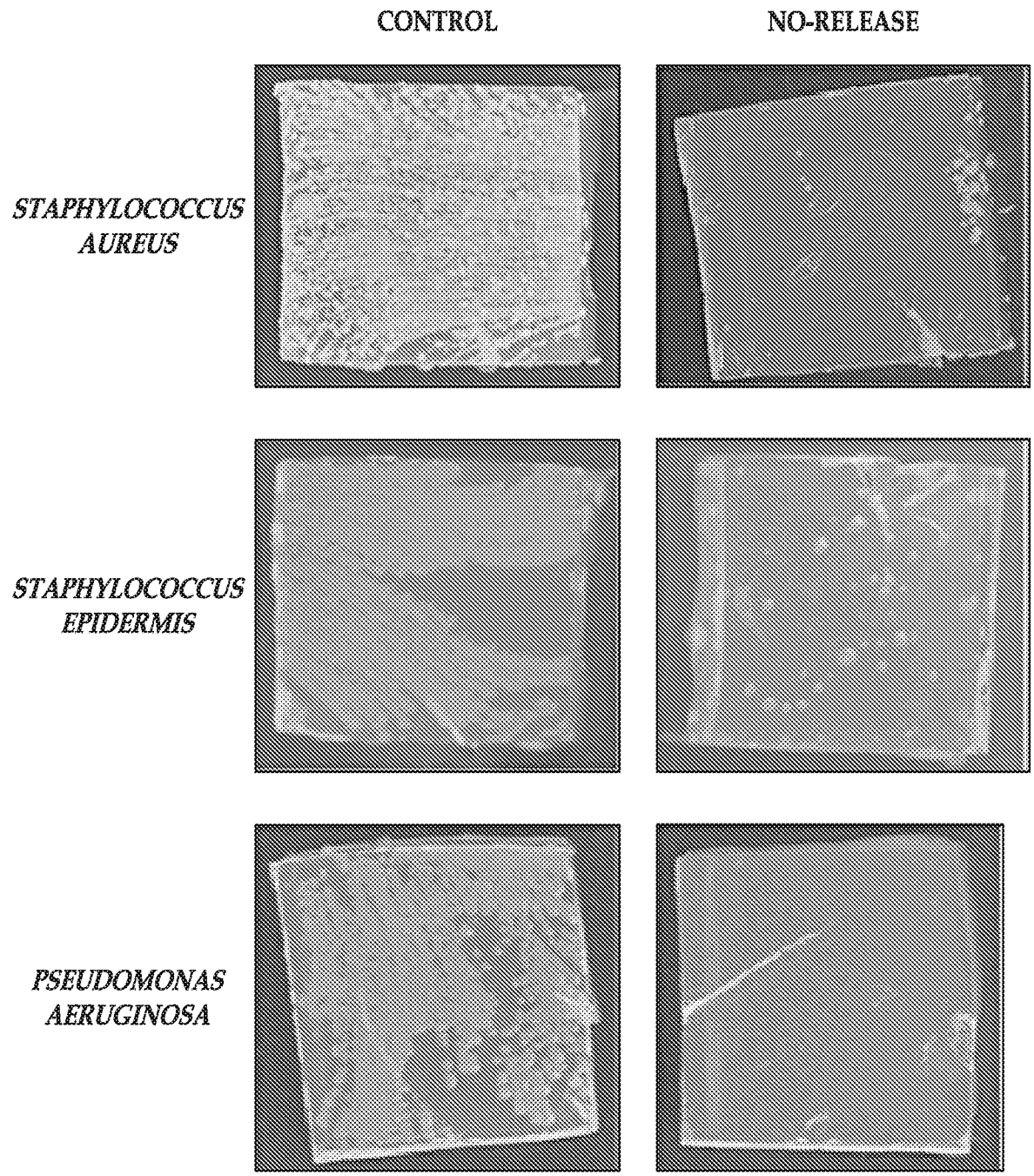
FIG. 13 depicts several black and white images (originals were in color) from an antimicrobial test for 3 strains of bacteria after 6 hours of incubation, where the samples included untreated control samples, and samples treated with a mixture of 11.5 wt % GSNO and 4 wt % $CuSO_4$ in NEOSPORIN®.

FIGS. 12 and 13 show the results of this time trial test. FIG. 12 shows the results for the first mixture (11.5 wt % GSNO and 4 wt % $CuSO_4$ in NEOSPORIN®) and FIG. 13 shows the results for the second mixture (the GSNO in VASELINE® and ZnO cream mixture (27.3:72.7)) The first mixture (including $CuSO_4$ in the cream) showed significant killing after 5 hours, while the second mixture (including ZnO) showed significant killing after 4 hours.

Figure 14:
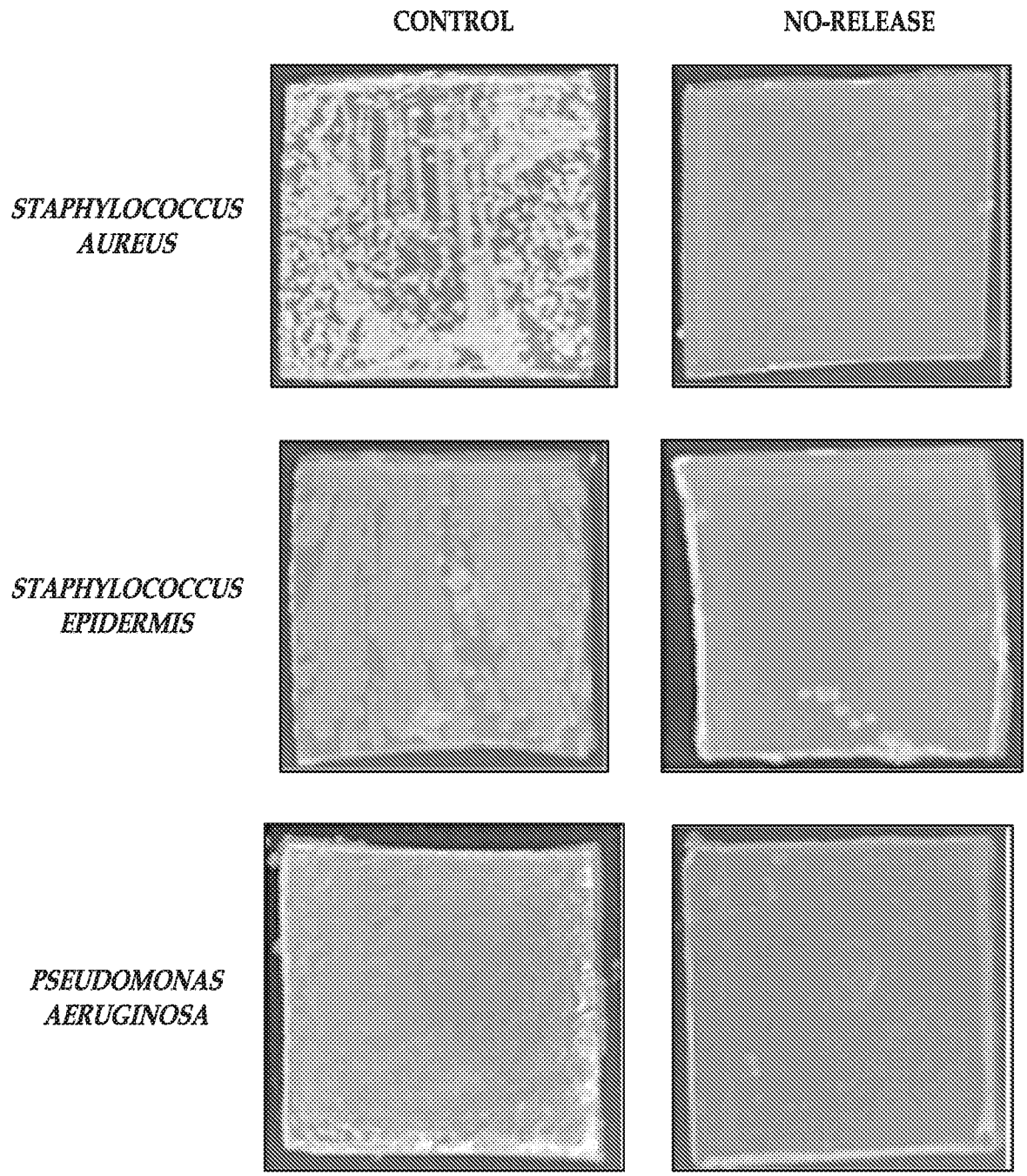
FIG. 14 depicts several black and white images (originals were in color) from an antimicrobial test for 3 strains of bacteria after 6 hours of incubation, where the samples included untreated control samples, and samples treated with a mixture of ZnO cream and GSNO/VASELINE®, where the final mixture included 9.1 wt % GSNO and 9.5 wt % ZnO.

The LB Agar plate test described in this example was also used for SNAP/ZnO systems. The SNAP formulation included a 50:50 mixture of 15 wt % SNAP in VASELINE® and 13% ZnO cream. The SNAP formulation was applied to a silicone membrane and then the membrane was placed on the piece of LB agar after inoculation with the bacteria strain. Incubation and growth were performed as described in this example. The results are shown in FIG. 14. The SNAP formulations were effective in killing each of the bacteria.

Figure 15:
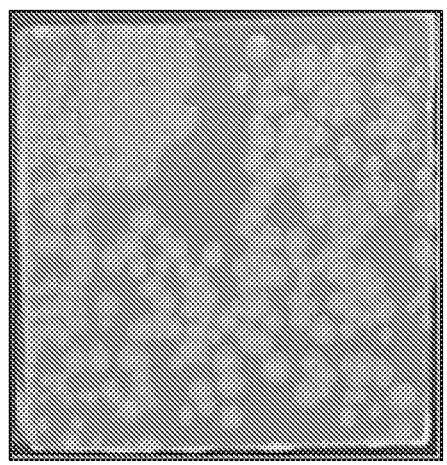
FIG. 15 depicts several black and white images (originals were in color) from an antimicrobial time test involving *Staphylococcus epidermis*, where the samples included an untreated control sample, and a sample treated with a mixture of 11.5 wt % GSNO and 4 wt % CuSO$_4$ in NEOSPORIN®.
Figure 15:
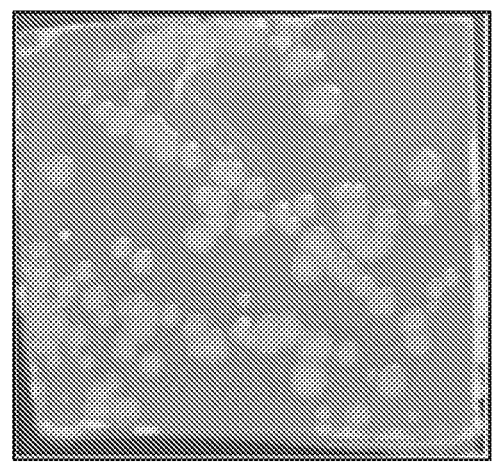
Figure 15:
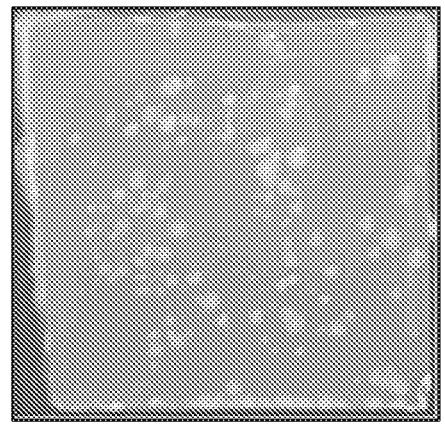
Figure 15:
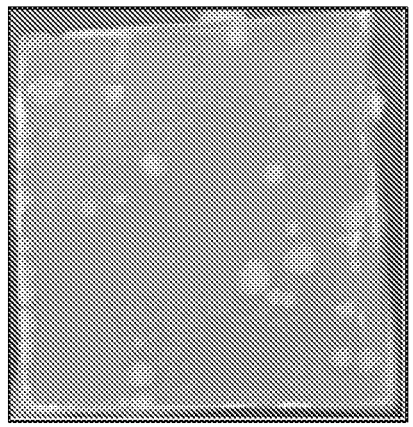
Figure 15:
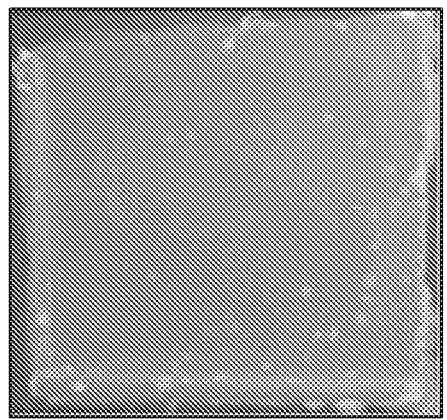
Figure 15:
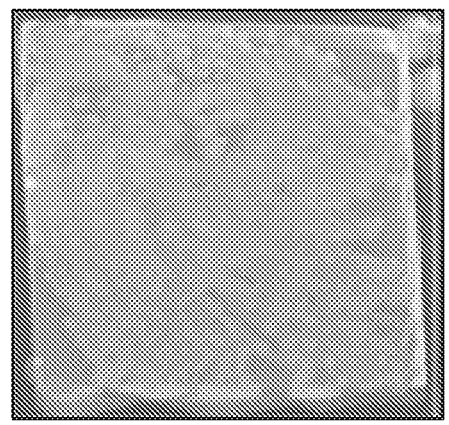

A third mixture (similar to the second mixture) was tested. This third mixture included a GSNO in VASELINE® and DESITIN® ZnO cream mixture (27.3:72.7) with 9.1 wt % GSNO and 9.5 wt % ZnO. This third mixture was tested as described in this example with strains of bacteria including *Staphylococcus epidermidis, Staphylococcus aureus, Pseudomonas aeruginosa*—each at a concentration of $10^5$ CFU/mL, and *Propionibacterium acnes* (*P. acnes*)—at a concentration of <$10^8$ CFU/mL. The results for the control samples and the mixtures are shown in FIG. 15. These results for the third mixture are similar to and even better than those shown in FIG. 11 (using the second mixture).

An antimicrobial study was performed to determine the average log reduction (n=2) of each bacteria strain over time using the third mixture. The results are shown in Table 6.

TABLE 6

| Strain | Log Reduction |
| --- | --- |
| staphylococcus epidermidis | 3.64 |
| staphylococcus aureus | 3.98 |
| pseudomonas aeruginosa | 3.70 |
| propionibacterium acnes | 3.82 |

Table 6 illustrates that a significant reduction in the viable counts of the four bacterial strains over 6 hours takes place when treated with the third mixture (one example of the mixture formed with the two-part topical composition disclosed herein).

Pig Skin Tests

Antimicrobial tests were also performed with pig skins.

The treatment protocol for the pig skins was as follows: 1. Pork with skin was purchased (the skin requirement: hairless, surface smooth, was not burned). 2. The skin was removed from the meat using a scalpel, and then preserved at −20° C. 3. The skin was cut into pieces according to experimental requirement (about 2×2 cm). 4. The skin surface was sterilized with alcohol wipes twice, and dried for 5 minutes under hood to remove alcohol on the surface.

5. 50 μL of diluted overnight culture of *S. aureus* (*Staphylococcus aureus*) (about 1×10^8 CFU/ml) was spread on the surface. 6. Respective mixtures were then applied on the top of skin surface by using a stencil razor blade. 7. The pig skin with cream was put into petri dish and incubated at 34° C. for 6 hours. 8. After an incubation time of 6 hours, the mixture was carefully removed by a razor blade. The skin was then tested for bacteria counts or microscopic observation. 9. For bacteria counts: the skin piece was put into 2 mL of 1×PBS buffer and homogenized thoroughly. PBS buffer was 10-fold serially diluted and 50 uL of each dilution was spread on an LB agar plate for incubation overnight. 10. For microscopic observation, the skin was stained with bacterial Live/Dead BacLit dyes for 15 minutes in the dark. Then, skin was observed by using fluorescent microscope with 60× lens.

With the pig skin test, the NO-release cream was a mixture including GSNO in VASELINE® and DESITIN® ZnO cream (at a weight ratio of 27.3:72.7) with 9.1 wt % GSNO and 9.5 wt % ZnO. The control cream was VASELINE® and DESITIN® ZnO cream (at a weight ratio of 27.3:72.7) (without any GSNO). No cream applied means the pig skin was inoculated with strain and no further manipulations made.

Table 7 shows the results of the bacteria counting method.

TABLE 7

| Sample | Total CFU/piece | Log Reduction |
| --- | --- | --- |
| No Cream Applied | 1.22E−09 | — |
| Control Cream | 1.08E−07 | 2.02 |
| NO-release Cream | 6.00E−04 | 4.27 (2.26) |

The control cream containing the ZnO (but without GSNO) showed a 2.02 log reduction compared to the no cream applied sample. The NO-release cream showed a 4.27 log reduction of bacteria compared to the no cream applied sample. This results in an additional 2.26 log reduction over that from the control cream.

Figure 16:
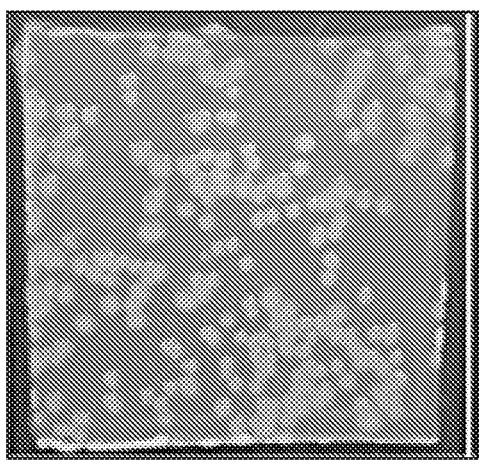
FIG. 16 depicts several black and white images (originals were in color) from an antimicrobial time test involving *Staphylococcus epidermis*, where the samples included an untreated control sample, and a sample treated with a mixture of ZnO cream and GSNO/VASELINE®, where the final mixture included 9.1 wt % GSNO and 9.5 wt % ZnO.
Figure 16:
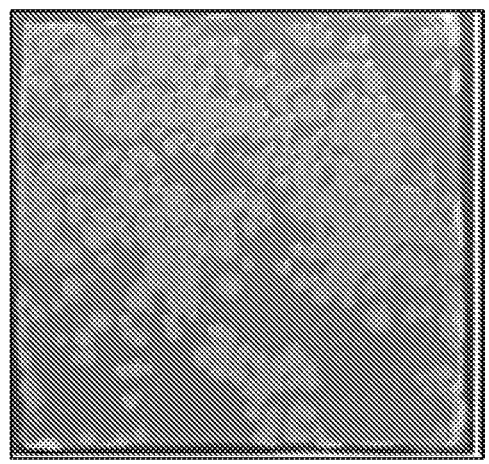
Figure 16:
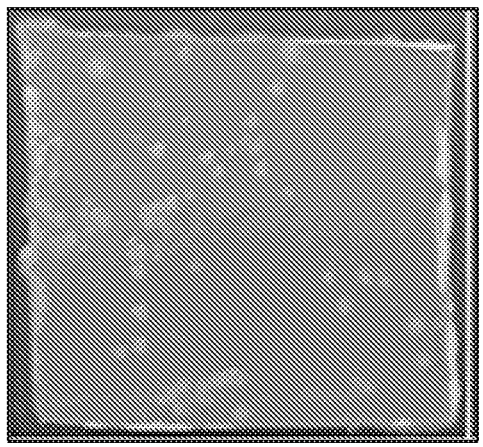
Figure 16:
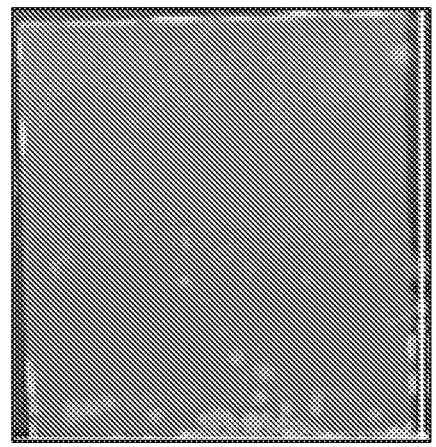
Figure 16:
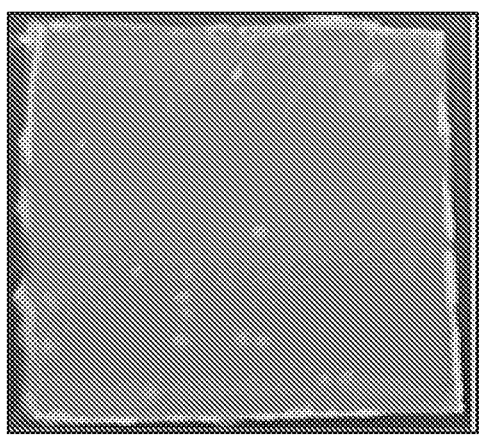
Figure 16:
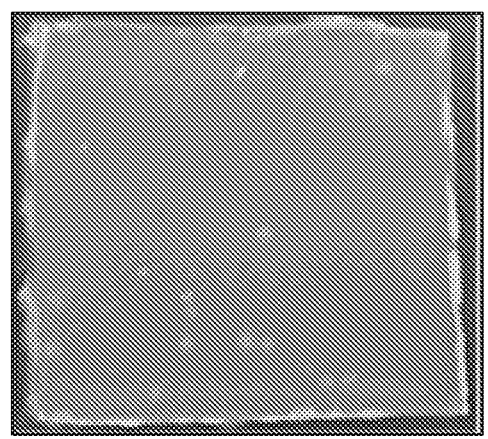
Figure 17:
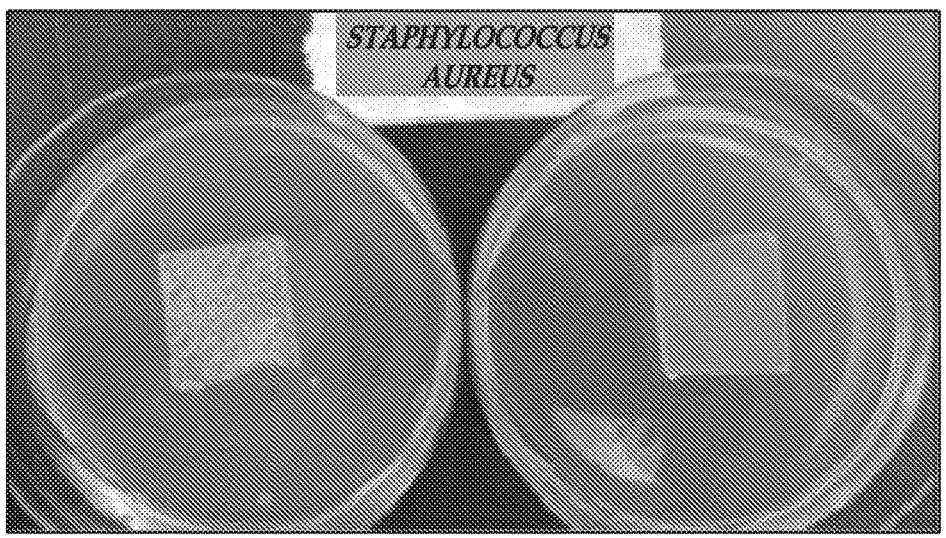
FIG. 17 depicts several black and white images (originals were in color) from an antimicrobial test for 3 strains of bacteria after 6 hours of incubation, where the samples included untreated control samples, and samples treated with a mixture of ZnO cream and SNAP/VASELINE®, where the final mixture included 7.5 wt % SNAP and 6.5 wt % ZnO.
Figure 17:
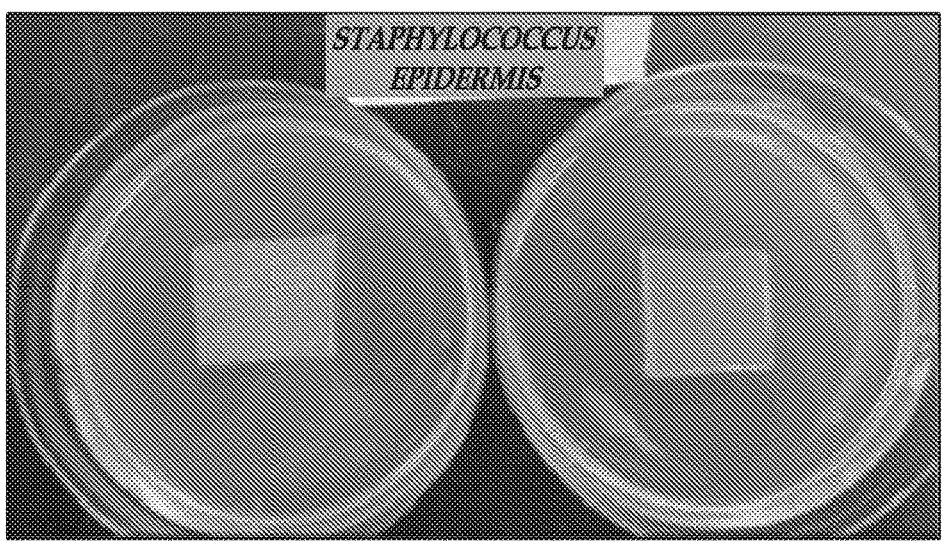
Figure 17:
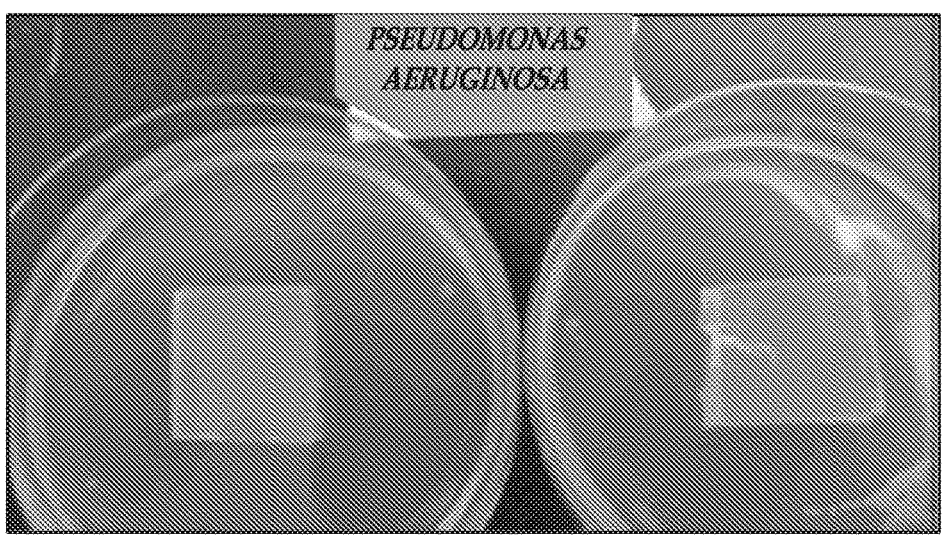
Figure 18:
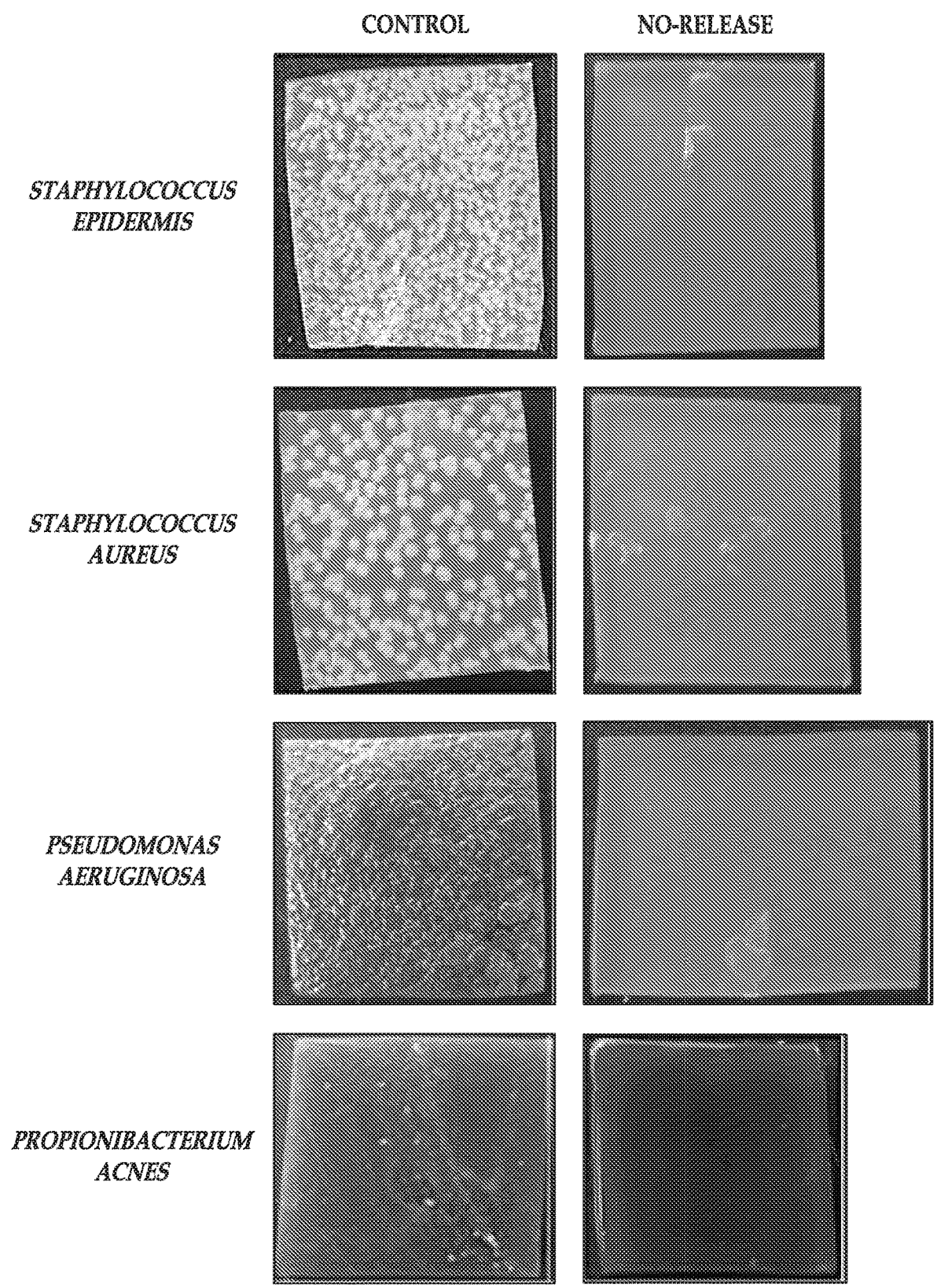
FIG. 18 depicts several black and white images (originals were in color) from an antimicrobial test for 3 strains of bacteria after 6 hours of incubation, where the samples included untreated control samples, and samples treated with a mixture of DESITIN® ZnO cream and GSNO/VASELINE®, where the final mixture included 9.1 wt % GSNO and 9.5 wt % ZnO.
Figure 19:
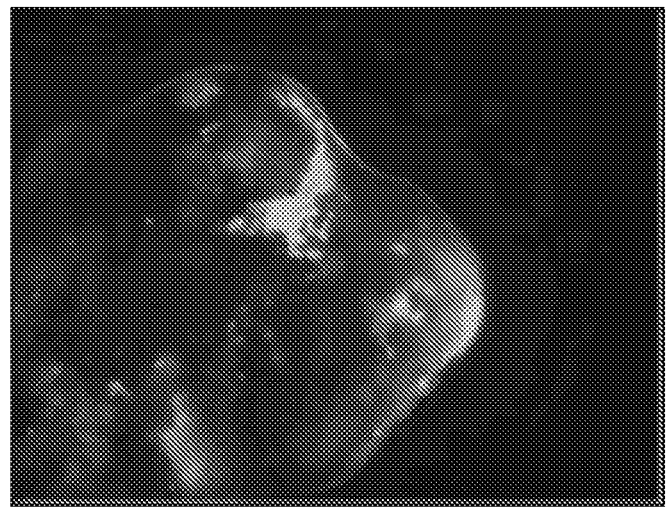
FIG. 19 depicts several black and white fluorescent microscopy images (originals were in color) from a antimicrobial pig skin study involving the use of no cream, an NO-releasing cream, and a control cream (including ZnO but no GSNO)
Figure 19:
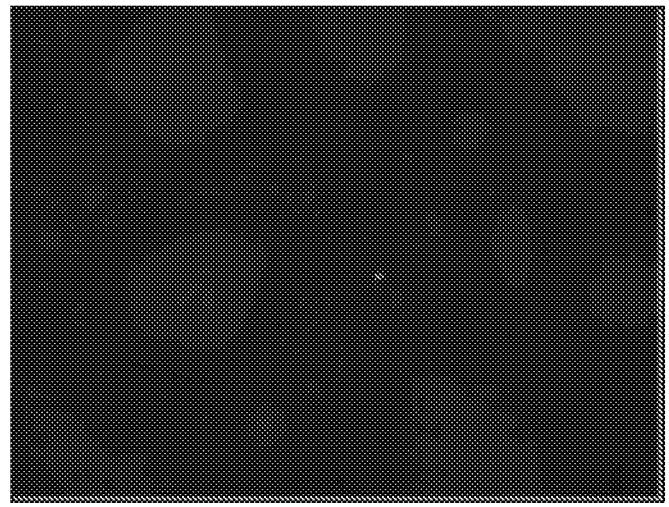
Figure 19:
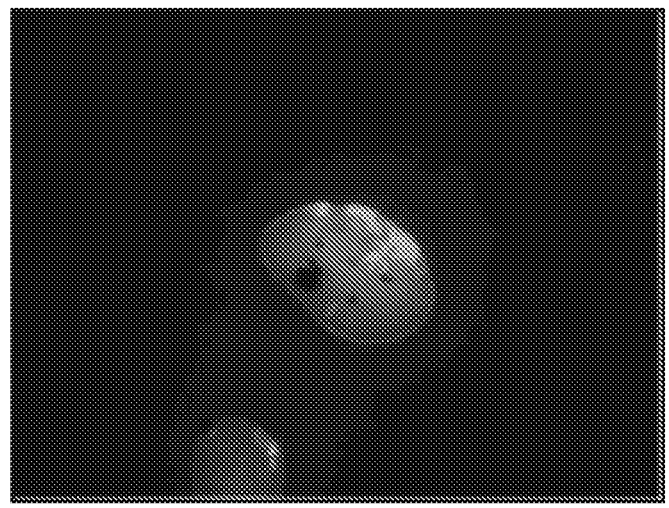

Fluorescent microscopic images were also taken of the pig skin samples. These images are shown in FIG. 16 and reveal that it is difficult to see any bacteria when the NO-releasing cream was applied. When the control cream (containing ZnO but no GSNO) was applied, bacteria still remained on skin surface and congregated in pockets/indentations within the pig skin.

Antimicrobial Involving SNAP

5% SNAP and 2.5% SNAP loaded ZnO creams were prepared. LB Agar plates were used in accordance with the method previously described for the first and second mixtures containing GSNO in VASELINE® and ZnO. In this test, DESITIN® was used. Table 8 shows the summary of cell counts from the agar plate models after 6 hours of incubation. Each plate was incubated with either no cream (i.e., control) (C0), DESITIN® ZnO cream (S0) on silicone rubber film, 2.5% SNAP in DESITIN® ZnO cream (S1) on film, or 5.0% SNAP in DESITIN® ZnO cream (S2) on film.

TABLE 8

| Strain | Sample | CFU/piece | Log | Log Reduction |
| --- | --- | --- | --- | --- |
| pseudomonas aeruginosa | C0 | 6.60E+03 | 3.82E+00 | — |
| pseudomonas aeruginosa | S0 | 1.40E+03 | 3.15E+00 | 6.73E−01 |
| pseudomonas aeruginosa | S1 | 1.00E+00 | 0.00E+00 | 2 |
| pseudomonas aeruginosa | S2 | 1.00E+00 | 0.00E+00 | 3.522879 |
| staphylococcus epidermidis | C0 | 1.40E+04 | 4.15E+00 | — |
| staphylococcus epidermidis | S0 | 2.80E+03 | 3.45E+00 | 6.99E−01 |
| staphylococcus epidermidis | S1 | 1.20E+02 | 2.08E+00 | 2.07E+00 |
| staphylococcus epidermidis | S2 | 6.00E+01 | 1.78E+00 | 2.37E+00 |

The log reductions for the 2.5% SNAP (half-dose) are greater than half of the log reductions for 5.0% SNAP. This suggests that the full 5.0% might not be necessary and is potentially less efficient than lower doses of SNAP.

Antimicrobial Involving Different GSNO Wt %

This experiment was completed to demonstrate the killing effect of NO released from the 3, 6, and 9 wt % GSNO test mixtures (described in Example 3 under NO Release Kinetics) with the DESITIN® cream containing 13% ZnO against *Staphylococcus aureus, Staphylococcus epidermidis*, and *Pseudomonas aeruginosa*. These 3 bacteria strains were chosen because they have shown to be common bacteria associated with wound or burn-wound infection.

Figure 20:
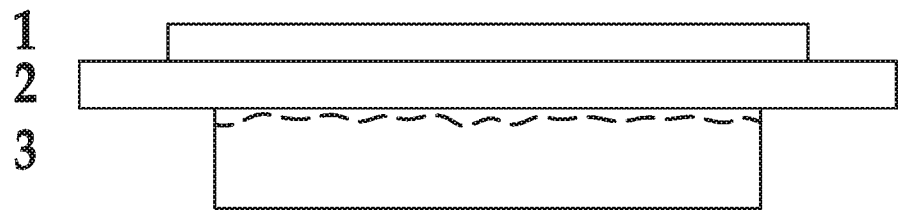
FIG. 20 is a schematic illustration of an experimental setup for an antimicrobial experiment involving GSNO/VASELINE® and zinc oxide mixtures with different wt % GSNO.

This experiment was performed using the schematic depicted in FIG. 20, where layer 1 was the tested mixture, layer 2 was a silicone sheet, layer 3 was an LB agar square, and the bacteria strain was positioned at the interface of 2 and 3. The silicone sheet (2) was used to keep the matrices (1) from coming into direct contact with the bacteria such that no matrix killing effects were observed. In these experiments, any observed bacteria killing came solely from the NO that diffuses through the silicone sheeting, and not from the ZnO antimicrobial activity. This antimicrobial experiment was completed in the dark at 34° C. with an incubation/application period of 6 hours.

Overnight grown bacteria cultures were diluted with 1×PBS buffer (10 mM, pH 7.2) to 1×105 CFU/mL. 50 μL of the diluted culture was spread on to a 6 cm diameter LB agar plate (layer 3 in FIG. 20) and allowed to air dry for about 10 minutes. Squares, 1.5 cm×1.5 cm, were cut from the inoculated LB agar and placed in an empty petri dish. Separately, medical grade silicone sheeting (0.0127 cm thick) (layer 2 in FIG. 20) was cut into 2.5 cm×2.5 cm squares. Using a plastic (polystyrene) stencil to define the matrices area (2 cm×2 cm×0.033 cm), different mixtures (e.g., GSNO at different wt % in VASELINE® mixed with commercial zinc oxide cream (with 13 wt % ZnO)) were spread onto the square silicone sheets (0.005" thick) and the excess was scraped away. The average mass of matrix on each silicone sheet was 84.9±3.0 mg (n=6). The square silicone sheets (layer 2) with the given matrix mixture (layer 1) were placed on top of the inoculated LB agar squares (layer 3) and the cover was lightly place on the petri dish. Samples were incubated at 34° C., absent from light, for about 6 hours. After incubation, the silicone sheets were removed from the top of the LB agar squares. A circle (diameter 0.8 cm) was punched out using a biopsy punch (Tru-punch, Fisher Scientific, Hampton, N.H.) from the center of the LB agar squares. This punched out circle was homogenized in 2 mL of 1×PBS (10 mM, pH 7.2) in a 15-mL tube using a homogenizer (OMNI TH, OMNI International, Kennesaw, GA) at full speed, and 10-fold serially diluted. 50 μL of the dilutions were spread on fresh LB agar plate for overnight culturing and single colonies were numerated.

Figure 21A:
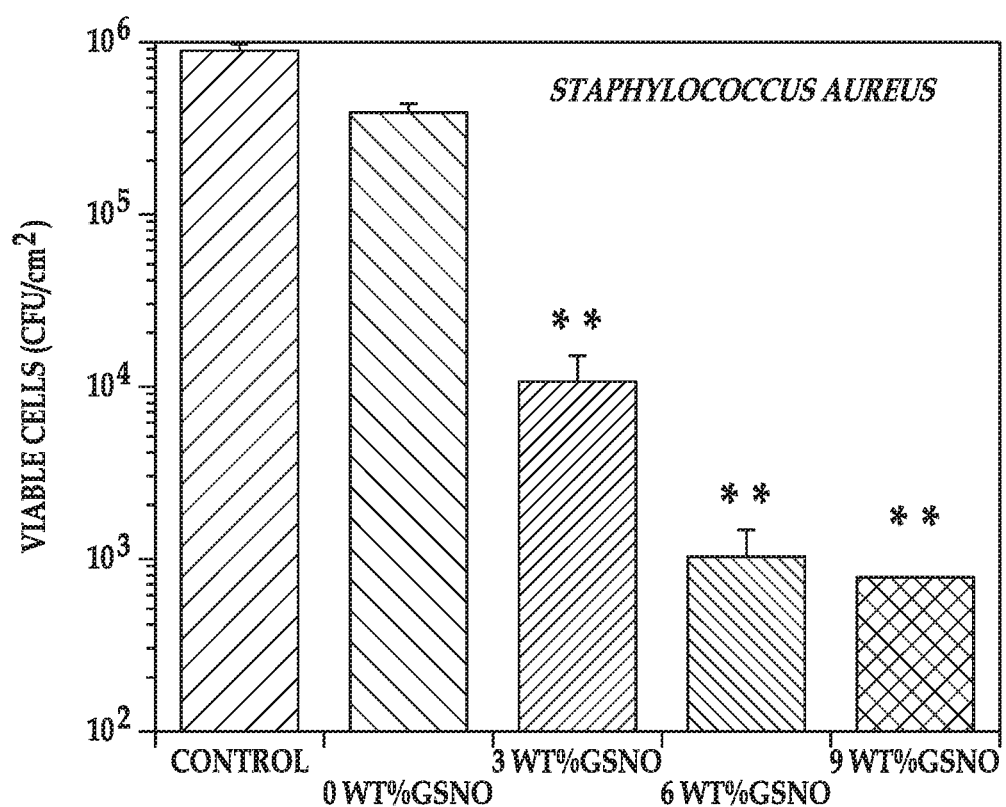
FIGS. 21A through 21C are graphs depicting the results for the antimicrobial experiment utilizing the experimental setup shown in FIG. 20 (no error bar means the LOD was reached for each trial; data represents the mean±SEM (n=3). * p<0.025, ** p<0.01, 0 wt % GSNO vs. 3, 6, and 9 wt % GSNO).
Figure 21B:
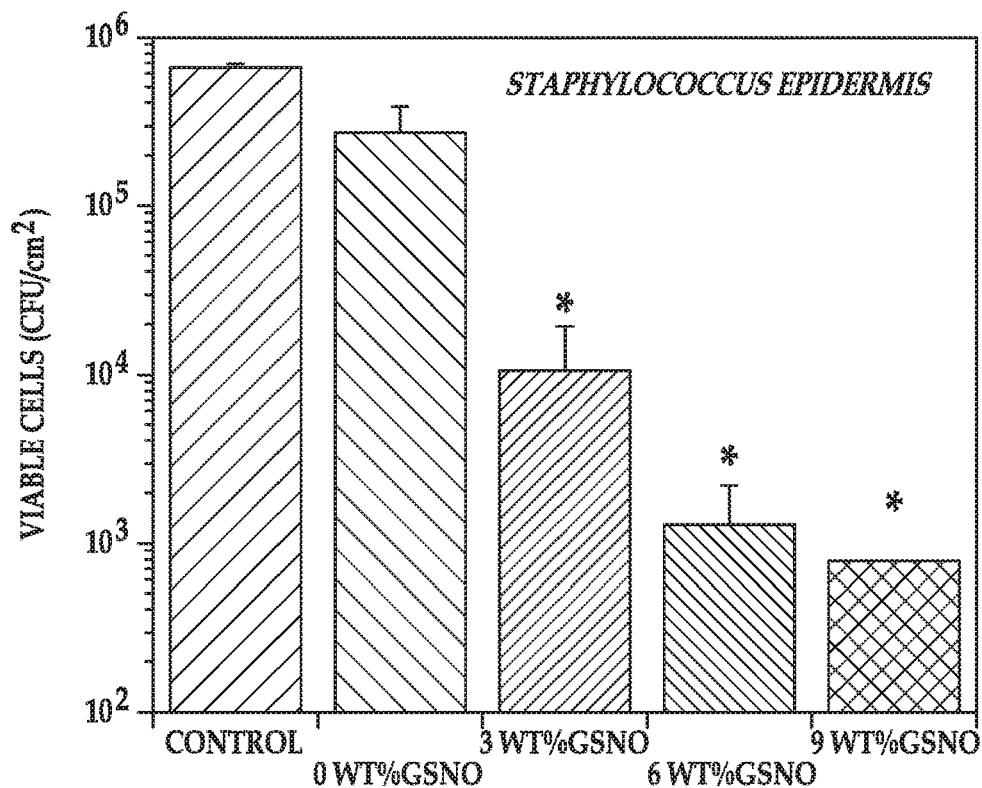
Figure 21C:
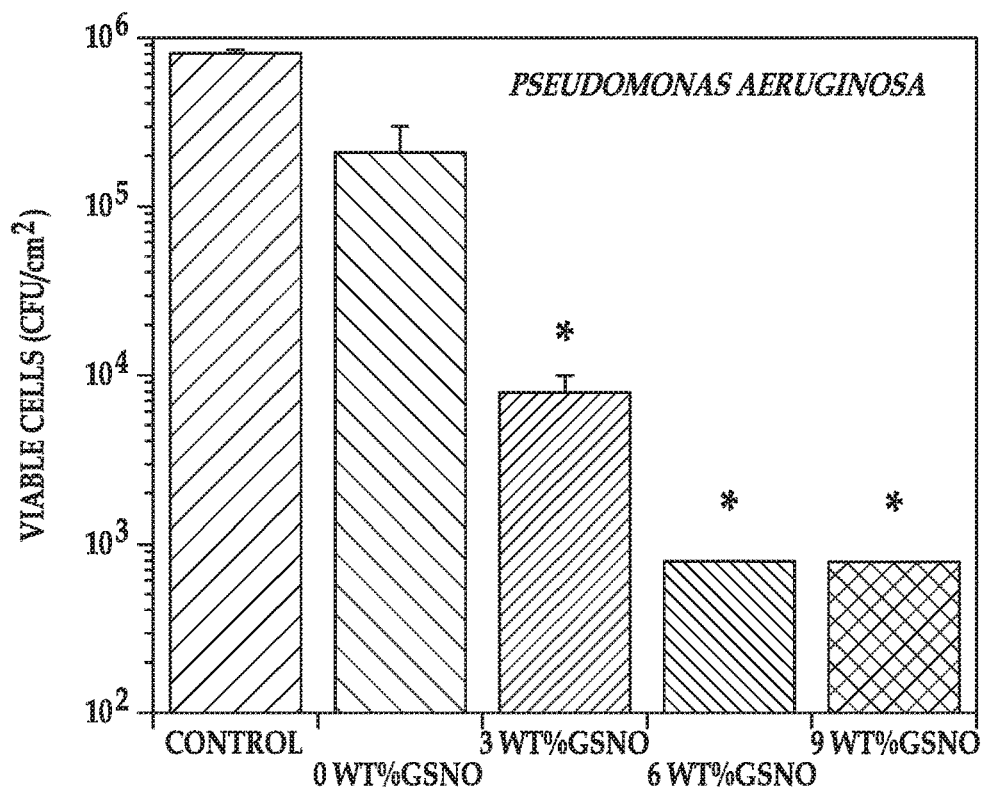

A control sample (labeled "Control" in FIGS. 21A-21C) was used. For this control sample, nothing was applied to the surface of the inoculated LB agar. The 0 wt % GSNO sample served as a second control to determine how much bacteria was lost when removing the silicone sheeting from the surface of the LB agar plate. From that level, any log reduction values were reported in the order *S. aureus, S. epidermidis, P. aeruginosa*. Comparing the "Control" columns in FIGS. 21A-21C versus the "0 wt % GSNO" columns in FIGS. 21A-21C, the average log reduction after removing the silicone sheeting was calculated to be 0.36 (for *S. aureus*), 0.37 (for *S. epidermidis*), and 0.57 (for *P. aeruginosa*). In FIG. 21A-21C, the columns that do not display an error bar killed all of the bacteria strain for each trial (n=3), therefore reaching the limit of detection (7.96 CFU/cm$^2$). The average log reduction between the 0 wt % GSNO and 3 wt % GSNO matrices were 1.55 (for *S. aureus*), 1.41 (for *S. epidermidis*), and 1.44 (for *P. aeruginosa*); between the 0 wt % GSNO and 6 wt % GSNO matrices were 2.56 (for *S. aureus*), 2.31 (for *S. epidermidis*), and 2.44 (for *P. aeruginosa*); and between the 0 wt % GSNO and 9 wt % GSNO matrices were 2.68 (for *S. aureus*), 2.53 (for *S. epidermidis*), and 2.44 (for *P. aeruginosa*).

In general, the amount of NO released from the 3, 6, and 9 wt % GSNO samples were able to kill each bacteria strain in a step-wise manner. One downside of this experiment was that the 9 wt % GSNO matrix always reached the limit of detection of the remaining live bacteria on the agar plate, and hence the step-wise killing effect was not as dramatic between the 6% and 9% GSNO formulations. Also, the matrix was not covered by any material, allowing NO to escape into the atmosphere and not come in contact with the bacteria. Nonetheless, these results demonstrate that NO produced from the ZnO enhanced reaction with GSNO is capable of killing both gram-positive (*S. aureus* and *S. epidermidis*) and gram-negative (*P. aeruginosa*) bacteria to a significant degree.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 10 wt % to about 20 wt % should be interpreted to include not only the explicitly recited limits of about 10 wt % to about 20 wt %, but also to include individual values, such as 13 wt %, 17.5 wt %, etc., and sub-ranges, such as from about 11 wt % to about 19 wt %, from about 14 wt % to about 18 wt %, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A two-part topical composition, comprising:
   a first composition including a S-nitrosothiol nitric oxide donor and a carrier, wherein the carrier includes petroleum jelly; and
   a second composition including zinc oxide, the second composition to be mixed with the first composition at a weight ratio of 50:50 to 80:20;
   wherein the zinc oxide is to react with the S-nitrosothiol nitric oxide donor at a temperature ranging from about 20° C. to about 40° C. to enhance a rate of release of nitric oxide from a mixture of the first composition and the second composition.

2. The two-part topical composition as defined in claim 1 wherein a concentration of the S-nitrosothiol nitric oxide donor in the first composition ranges from about 2.5 wt % to about 40 wt %.

3. The two-part topical composition as defined in claim 1 wherein a concentration of the zinc oxide in the second composition ranges from about 5 wt% to about 40 wt %.

4. The two-part topical composition as defined in claim 1 wherein:
   the S-nitrosothiol nitric oxide donor is selected from the group consisting of S-nitroso-N-acetyl-penicillamine, S-nitrosoglutathione, and combinations thereof; and
   the carrier is the petroleum jelly.

5. The two-part topical composition as defined in claim 1 wherein the second composition further includes mineral oil, petrolatum, beeswax, dimethicone, sorbitan sesquioleate, microcrystalline wax, PEG-30 dipolyhydroxy stearate, aloe barbadensis leaf extract, glycerin, tropolone, tocopheryl acetate, 1,2-hexanediol, caprylyl glycol, magnesium sulfate, potassium hydroxide, and phenoxyethanol.

6. The two-part topical composition as defined in claim 1 wherein the second composition further comprises a copper catalyst or an organoselenium catalyst.

7. A topical composition kit, comprising:
   a first container having therein a first composition including a S-nitrosothiol nitric oxide donor and a carrier, wherein the carrier includes petroleum jelly; and
   a second container having therein a second composition including zinc oxide, the second composition to be mixed with the first composition at a weight ratio of 50:50 to 80:20;
   wherein the first and second containers respectively deliver effective amounts of the first and second compositions, wherein the zinc oxide reacts with the S-nitrosothiol nitric oxide donor at a temperature ranging from about 20° C. to about 40° C. to enhance a rate of release of nitric oxide from a mixture of the first composition and the second composition.

8. The topical composition kit as defined in claim 7 wherein the second composition further includes mineral oil, petrolatum, beeswax, dimethicone, sorbitan sesquioleate, microcrystalline wax, PEG-30 dipolyhydroxystearate, aloe barbadensis leaf extract, glycerin, tropolone, tocopheryl acetate, 1,2-hexanediol, caprylyl glycol, magnesium sulfate, potassium hydroxide, and phenoxyethanol.

9. The topical composition kit as defined in claim 7 wherein the effective amounts of the first composition to the second composition correspond to the weight ratio.

10. The topical composition kit as defined in claim 7 wherein a concentration of the S-nitrosothiol nitric oxide donor in the first composition ranges from about 2.5 wt % to about 40 wt %.

11. The topical composition kit as defined in claim 7 wherein a concentration of the zinc oxide in the second composition ranges from about 5 wt % to about 40 wt %.

12. The topical composition kit as defined in claim 7 wherein:
the S-nitrosothiol nitric oxide donor is selected from the group consisting of S-nitroso-N-acetyl-penicillamine, S-nitrosoglutathione, and combinations thereof; and
the carrier is the petroleum jelly.

13. A method for regulating nitric oxide release from a topical composition, the method comprising:
mixing an effective amount of a first composition including a S-nitrosothiol nitric oxide donor and a carrier that includes petroleum jelly with an effective amount of a second composition including zinc oxide to form a mixture, the effective amounts of the first composition to the second composition correspond to a weight ratio ranging from about 50:50 to about 20:80; and
heating the mixture to a temperature ranging from about 20° C. to about 40° C.

14. The method as defined in claim 13 wherein:
a concentration of the S-nitrosothiol nitric oxide donor in the first composition ranges from about 2.5 wt % to about 40 wt %.

15. The method as defined in claim 13 wherein:
the S-nitrosothiol nitric oxide donor is selected from the group consisting of S-nitroso-N-acetyl-penicillamine, S-nitrosoglutathione, and combinations thereof; and
the carrier is the petroleum jelly.

16. A method for treating a skin ailment, the method comprising:
mixing an effective amount of a first composition including a S-nitrosothiol nitric oxide donor and a carrier that includes petroleum jelly with an effective amount of a second composition including zinc oxide to form a mixture, the effective amounts of the first composition to the second composition correspond to a weight ratio ranging from about 50:50 to about 20:80; and
applying the mixture to skin, whereby the mixture is heated to a temperature ranging from about 20° C. to about 40° C. and the zinc oxide reacts with the S-nitrosothiol nitric oxide donor to enhance a rate of release of nitric oxide.

17. The two-part topical composition as defined in claim 1 wherein the carrier further includes an ointment containing bacitracin, neomycin, and polymyxin B in a base of cocoa butter, cotton seed oil, sodium pyruvate, tocopheryl acetate, and additional petroleum jelly.

18. The topical composition kit as defined in claim 7 wherein the carrier further includes an ointment containing bacitracin, neomycin, and polymyxin B in a base of cocoa butter, cotton seed oil, sodium pyruvate, tocopheryl acetate, and additional petroleum jelly.

19. The method as defined in claim 13 wherein the carrier further includes an ointment containing bacitracin, neomycin, and polymyxin B in a base of cocoa butter, cotton seed oil, sodium pyruvate, tocopheryl acetate, and additional petroleum jelly.

* * * * *